(12) United States Patent
Maroscheck et al.

(10) Patent No.: US 10,098,730 B2
(45) Date of Patent: Oct. 16, 2018

(54) INJECTOR FOR IMPLANTING AN INTRAOCULAR LENS

(75) Inventors: Christoph Maroscheck, Hamburg (DE); Helmut Binder, Berlin (DE)

(73) Assignee: IOLUTION GMBH, Hamburg (DE)

( * ) Notice: Subject to any disclaimer, the term of this patent is extended or adjusted under 35 U.S.C. 154(b) by 707 days.

(21) Appl. No.: 14/118,257

(22) PCT Filed: May 15, 2012

(86) PCT No.: PCT/DE2012/000501
§ 371 (c)(1),
(2), (4) Date: Jan. 28, 2014

(87) PCT Pub. No.: WO2012/155887
PCT Pub. Date: Nov. 22, 2012

(65) Prior Publication Data
US 2014/0135784 A1    May 15, 2014

(30) Foreign Application Priority Data
May 18, 2011  (DE) .......................... 10 2011 101 940

(51) Int. Cl.
*A61F 2/16*    (2006.01)
(52) U.S. Cl.
CPC ............ *A61F 2/1678* (2013.01); *A61F 2/167* (2013.01); *A61F 2/1662* (2013.01)
(58) Field of Classification Search
CPC ...... A61F 2/167; A61F 2/1662; A61F 2/1678; A61F 2/1664; A61F 2/1667; A61F 2/1672; A61F 2/1675
See application file for complete search history.

(56) References Cited

U.S. PATENT DOCUMENTS

| | | | | |
|---|---|---|---|---|
| 5,123,905 A | * | 6/1992 | Kelman | A61F 2/1678 604/15 |
| 5,944,725 A | * | 8/1999 | Cicenas | A61F 2/1678 606/107 |
| 6,497,708 B1 | * | 12/2002 | Cumming | A61F 2/1664 606/107 |
| 6,607,537 B1 | * | 8/2003 | Binder | A61F 2/167 606/107 |

(Continued)

FOREIGN PATENT DOCUMENTS

WO    2000/045746    8/2000

*Primary Examiner* — Christopher L Templeton
(74) *Attorney, Agent, or Firm* — Occhiuti & Rohlicek LLP

(57) ABSTRACT

An injector system for implanting an intraocular lens into an eye includes an injector body having a front and rear ends; a cannula arranged at the front end, which provides a transport channel for a lens to be implanted; a magazine with a receptacle area for a lens which is securable in the receptacle area by a retainer, the magazine being arranged so that a lens can be fed into the transport channel via the preferably lateral inlet opening; a folding body insertable into the magazine and into the inlet opening, for pushing the lens into the transport channel in a manner so that the lens is partially foldable around the folding body; and a slider which is slideably arranged in the injector body and which can be pushed into the transport channel via the front end so that the lens can be ejected from the transport channel.

24 Claims, 25 Drawing Sheets

(56) References Cited

U.S. PATENT DOCUMENTS

| | | | |
|---|---|---|---|
| 2001/0020171 A1* | 9/2001 | Heyman | A61F 2/167 606/107 |
| 2002/0082609 A1* | 6/2002 | Green | A61F 2/1691 606/107 |
| 2003/0212406 A1 | 11/2003 | Kobayashi et al. | |
| 2003/0212408 A1* | 11/2003 | Kenichi | A61F 2/1678 606/107 |
| 2004/0243141 A1 | 12/2004 | Brown et al. | |
| 2005/0149056 A1* | 7/2005 | Rathert | A61F 2/1664 606/107 |
| 2005/0222577 A1* | 10/2005 | Vaquero | A61F 2/1678 606/107 |
| 2006/0155299 A1* | 7/2006 | Waldock | A61F 2/167 606/107 |
| 2007/0052923 A1* | 3/2007 | Ayyagari | A61F 2/1664 351/159.73 |
| 2008/0147081 A1* | 6/2008 | Pynson | A61F 2/1678 606/107 |
| 2008/0221584 A1* | 9/2008 | Downer | A61F 2/1678 606/107 |
| 2009/0043313 A1 | 2/2009 | Ichinohe et al. | |
| 2009/0131953 A1* | 5/2009 | Quintin | A61F 2/1678 606/107 |
| 2009/0204122 A1 | 8/2009 | Ichinohe et al. | |
| 2009/0292294 A1 | 11/2009 | Tanaka | |
| 2009/0318933 A1* | 12/2009 | Anderson | A61F 2/1664 606/107 |
| 2010/0010498 A1* | 1/2010 | Biddle | A61F 2/1664 606/107 |
| 2010/0256651 A1* | 10/2010 | Jani | B29C 59/16 606/107 |
| 2010/0312255 A1* | 12/2010 | Satake | A61F 2/1664 606/107 |
| 2011/0144653 A1* | 6/2011 | Pankin | A61F 2/1678 606/107 |
| 2011/0190777 A1* | 8/2011 | Hohl | A61F 2/1691 606/107 |
| 2011/0213380 A1* | 9/2011 | Han | A61F 2/167 606/107 |
| 2012/0221102 A1* | 8/2012 | Tanaka | A61F 2/167 623/6.12 |

\* cited by examiner

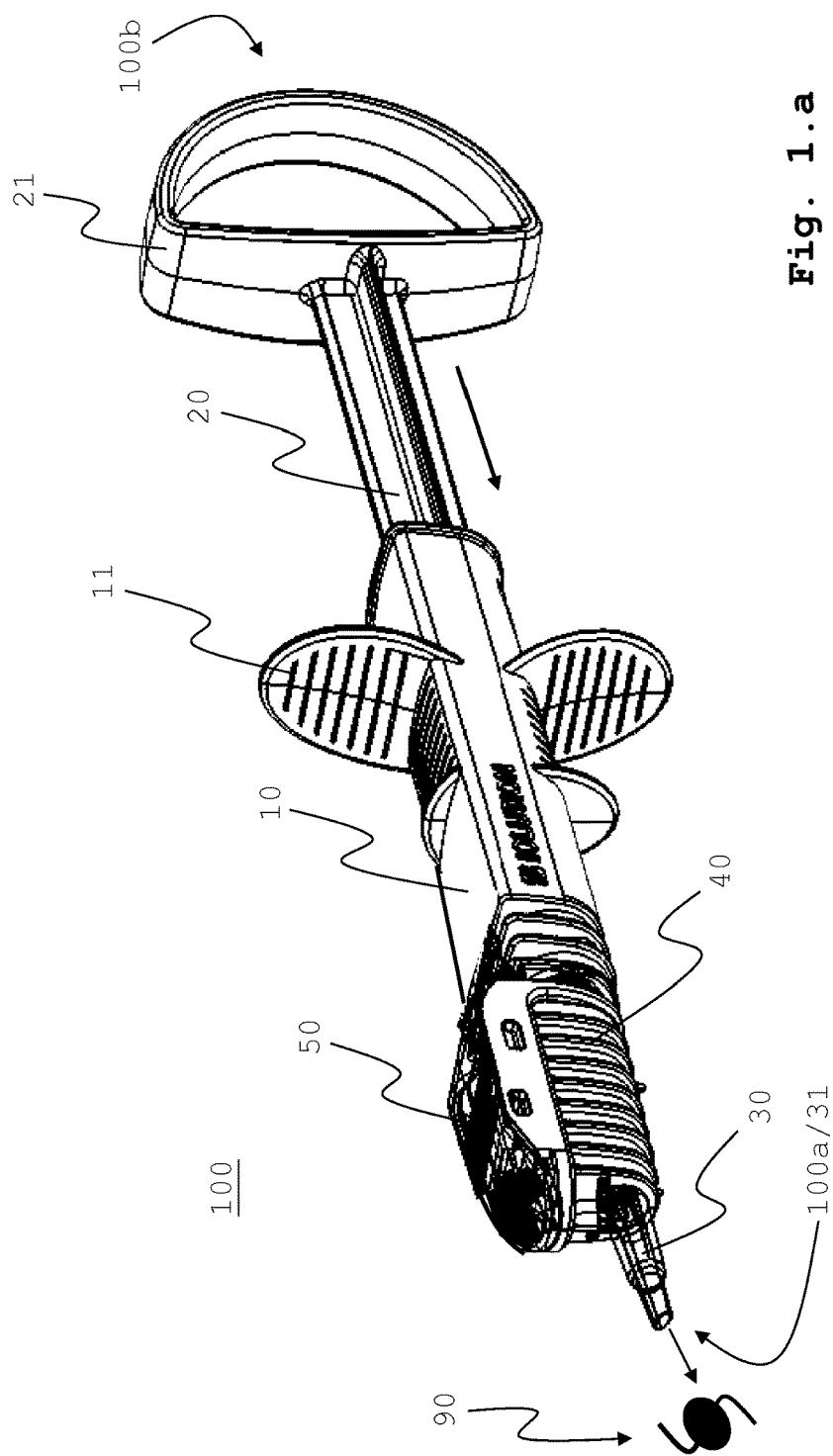

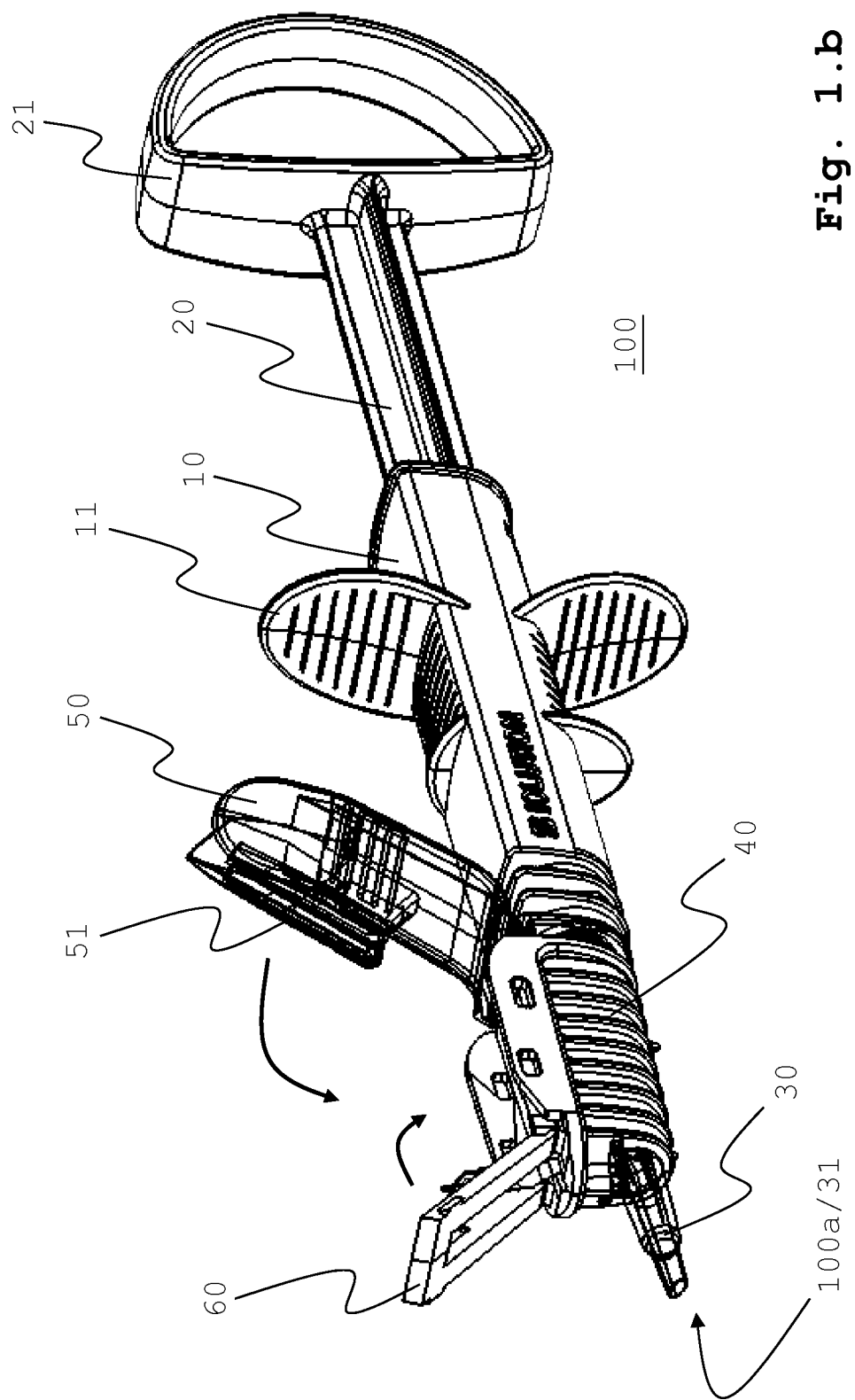
Fig. 1.b

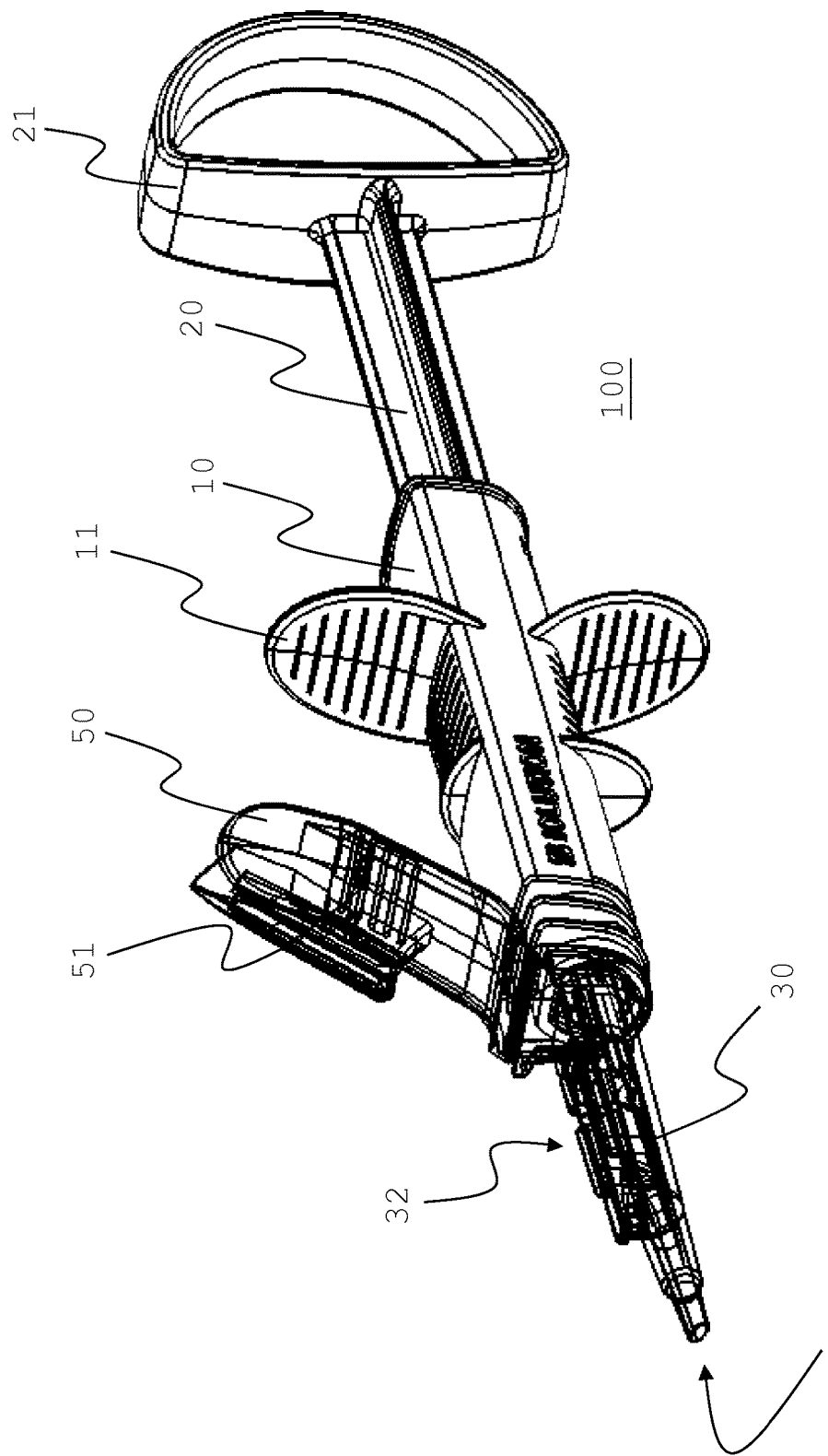
Fig. 1.c

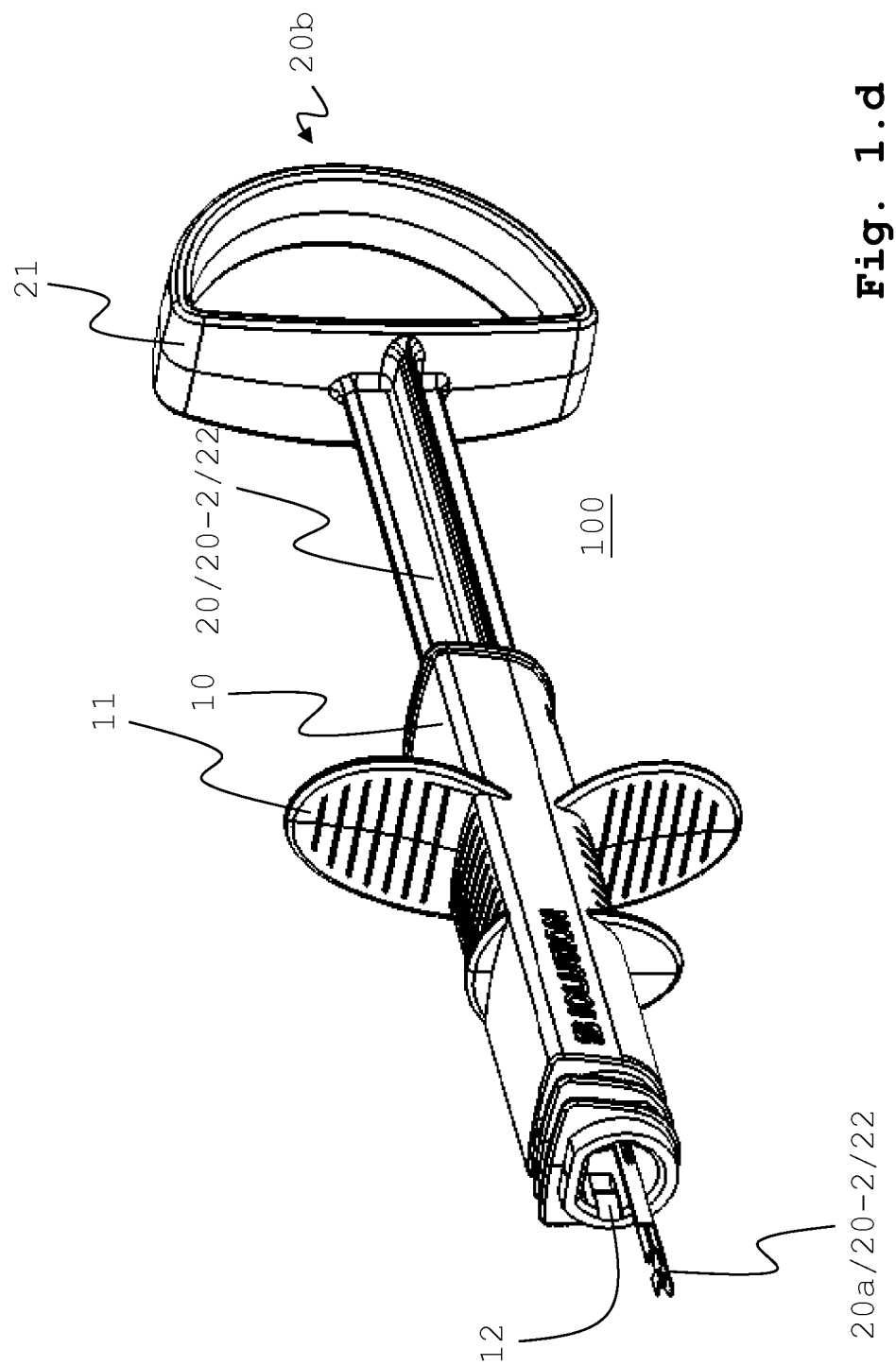
Fig. 1.d

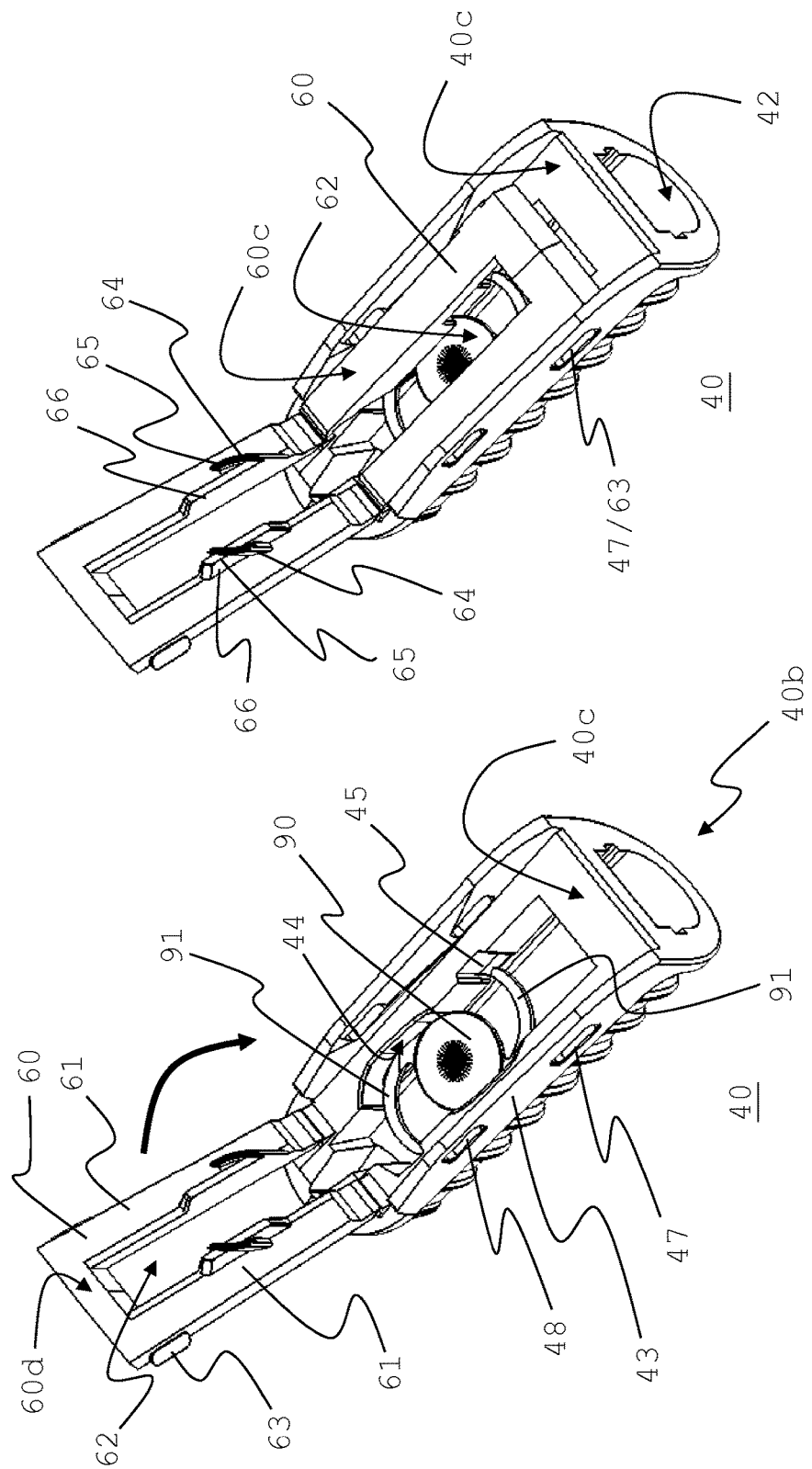

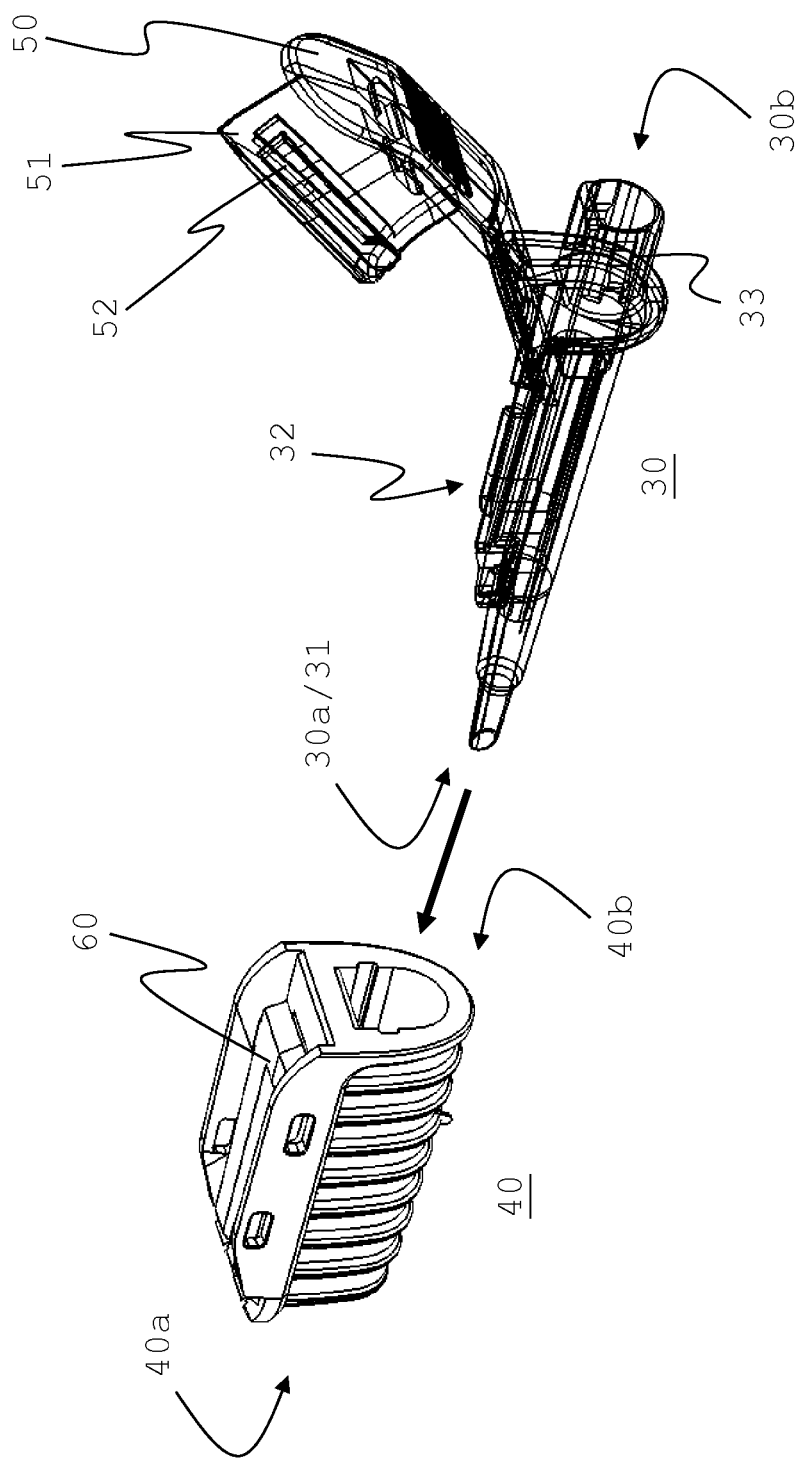

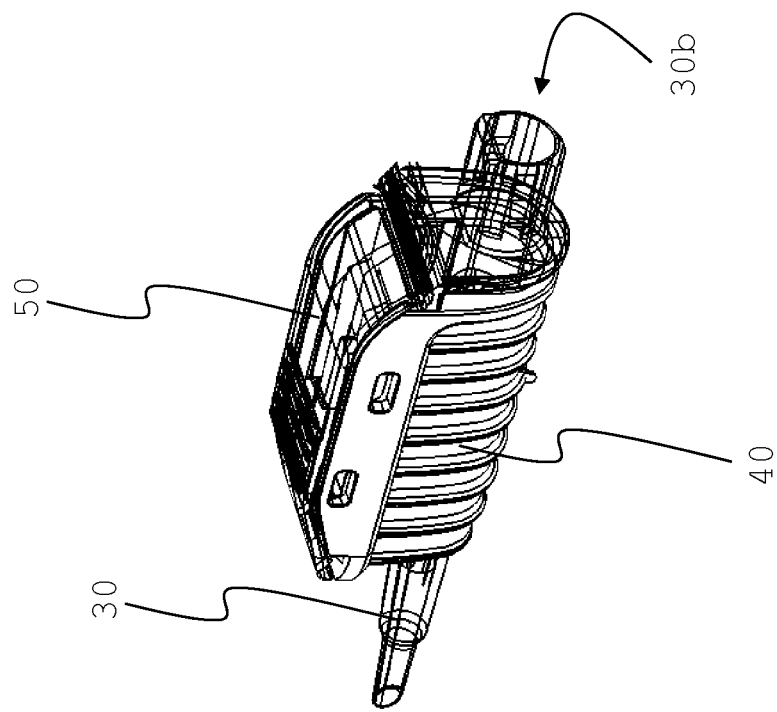
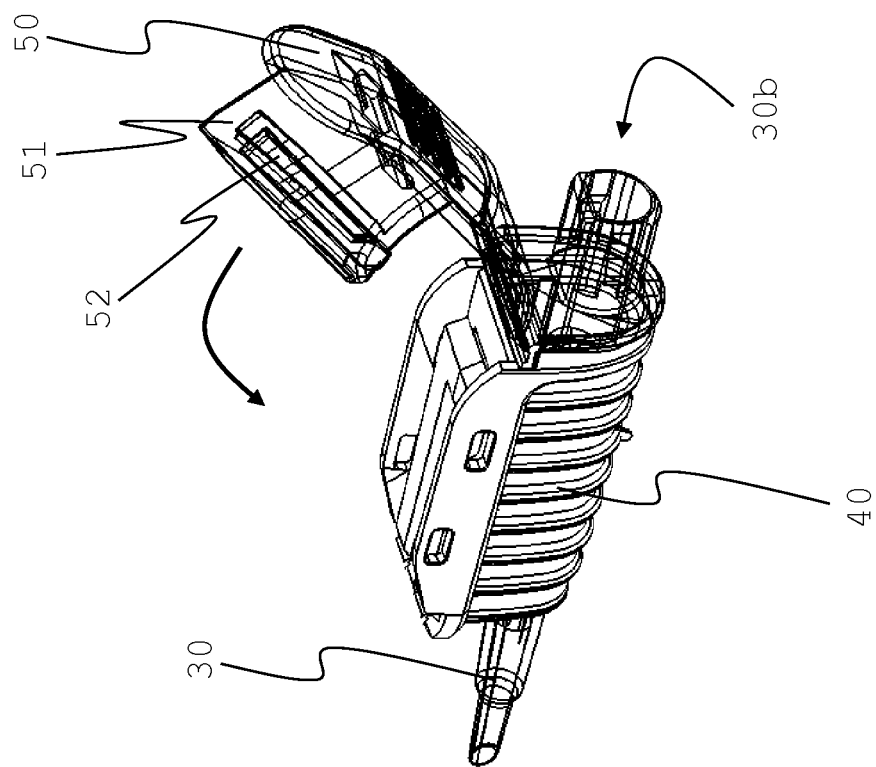
Fig. 3.d
Fig. 3.c

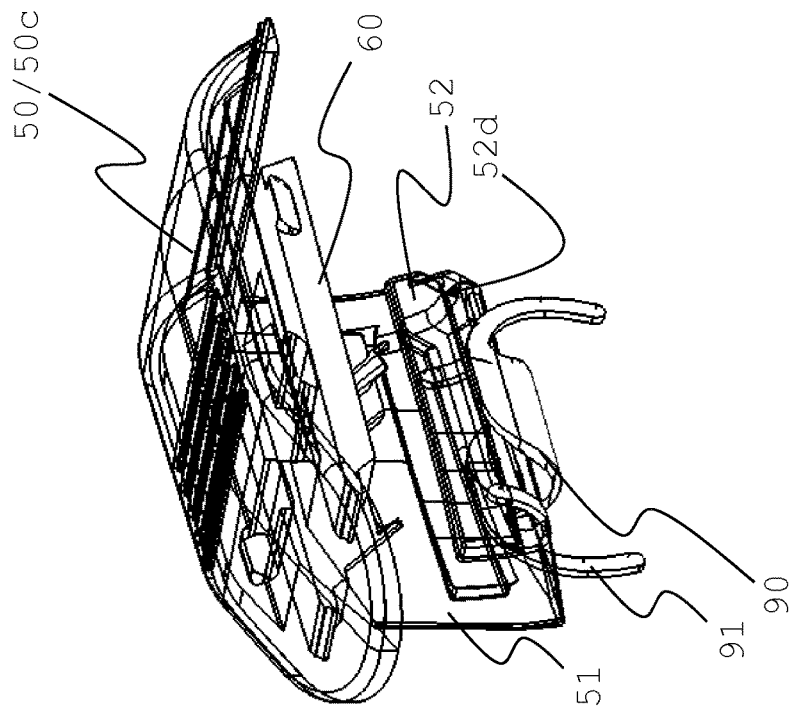
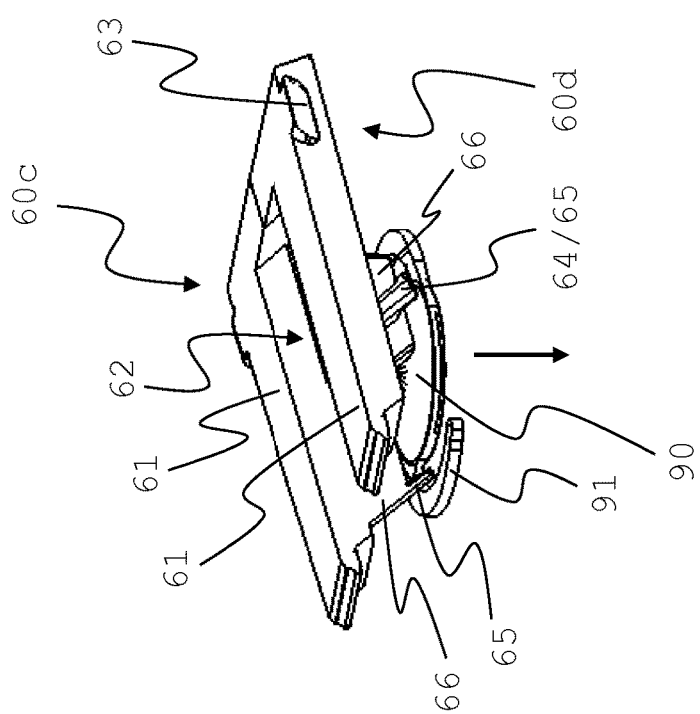
Fig. 4.b
Fig. 4.a

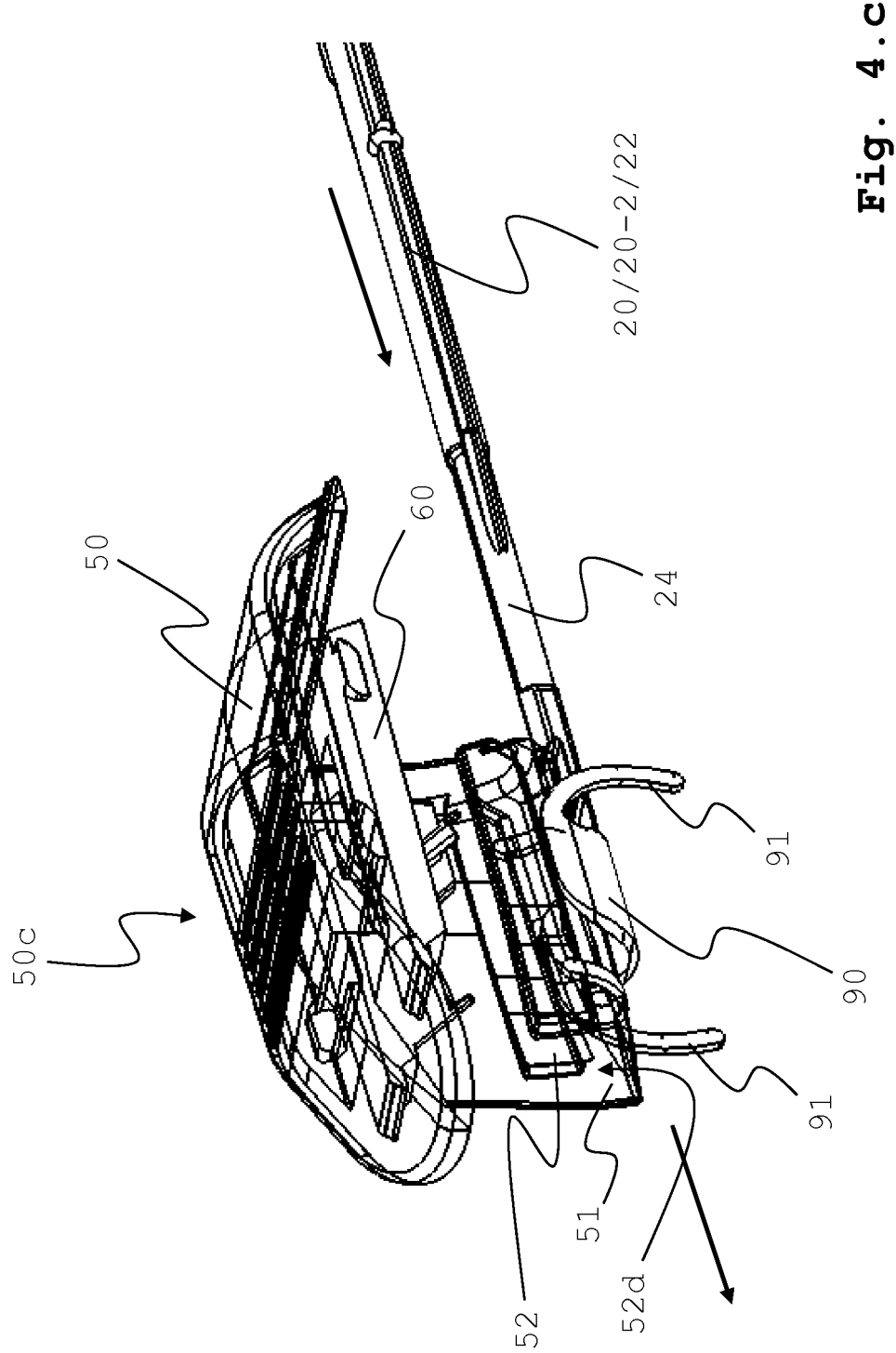
Fig. 4.c

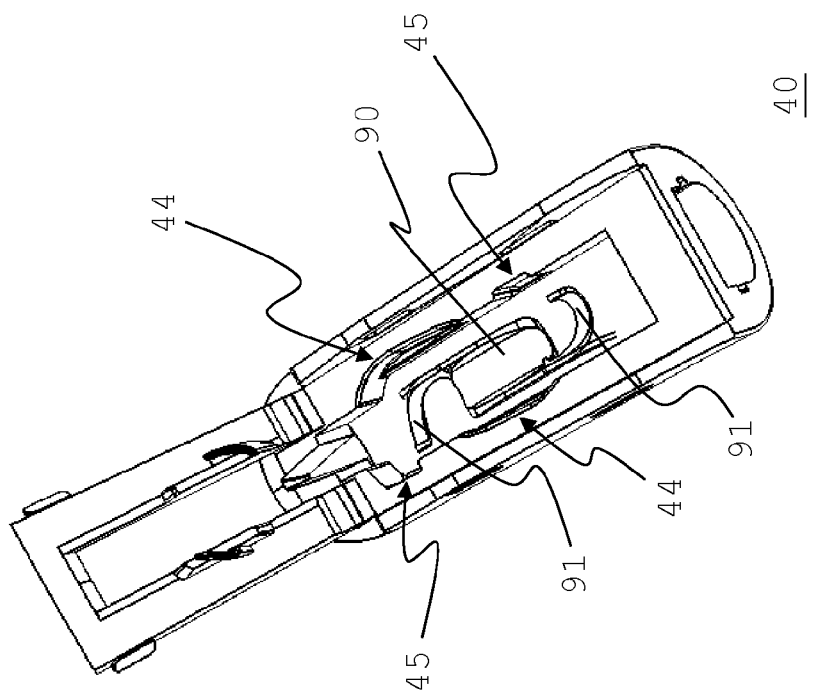
Fig. 5.b
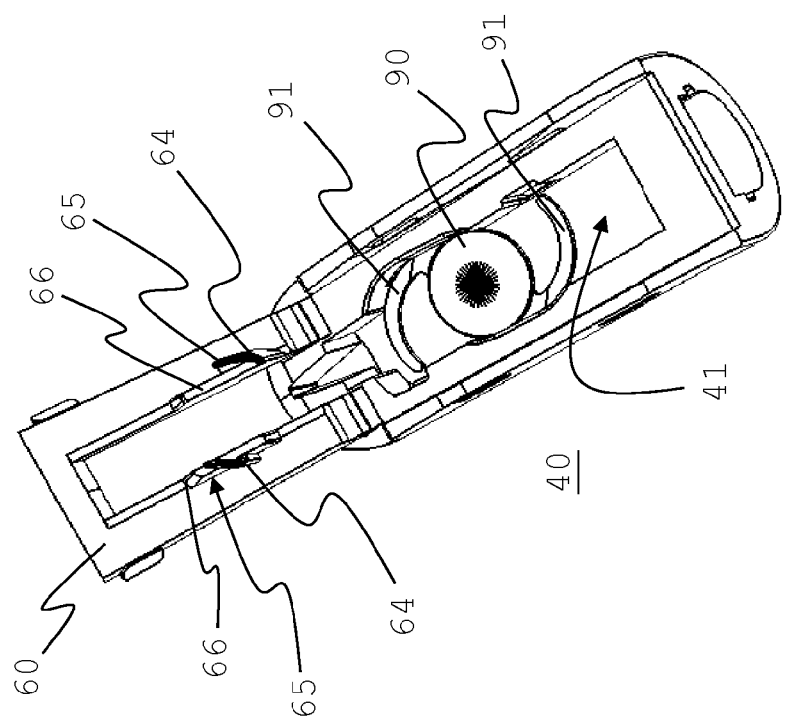
Fig. 5.a

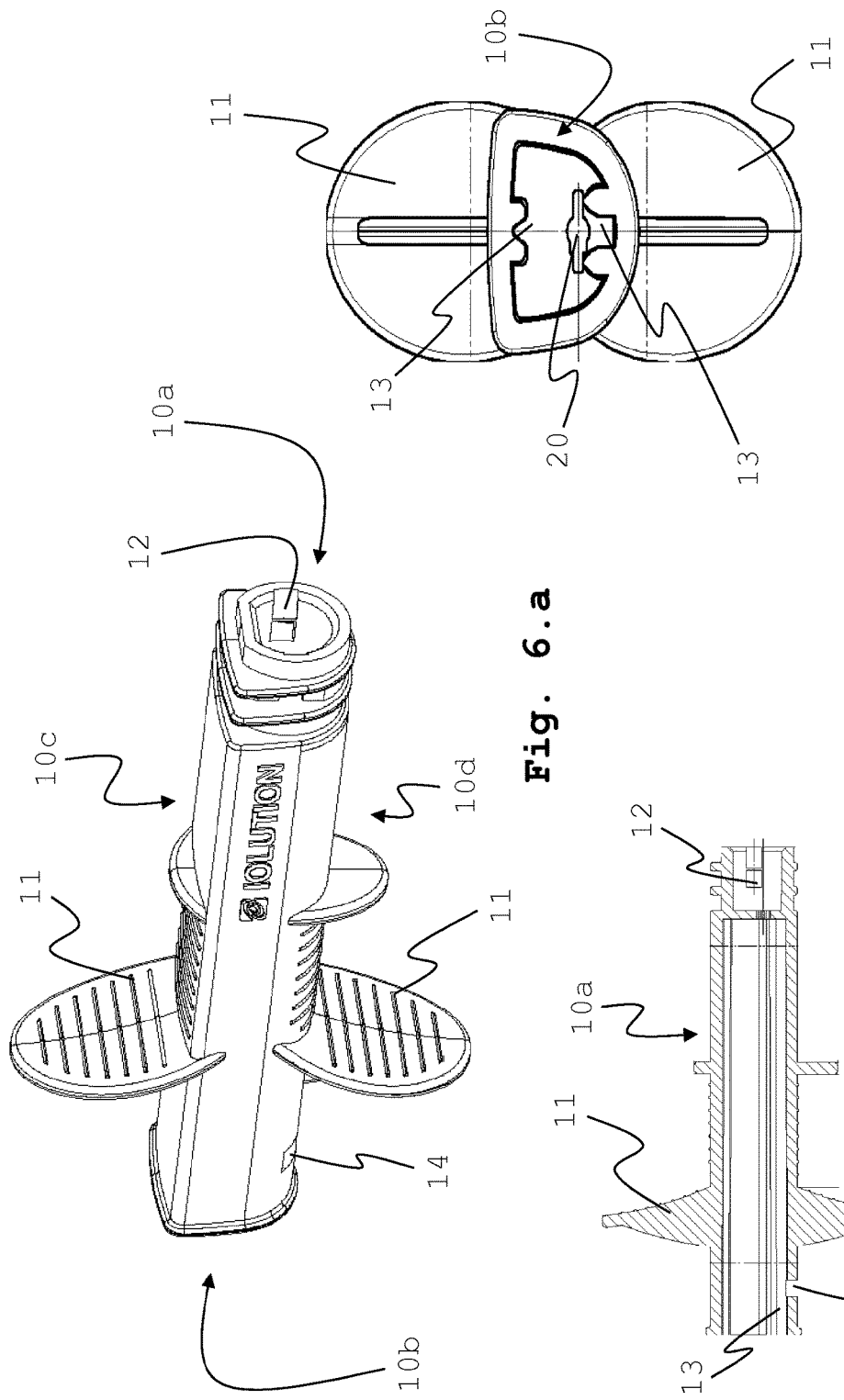

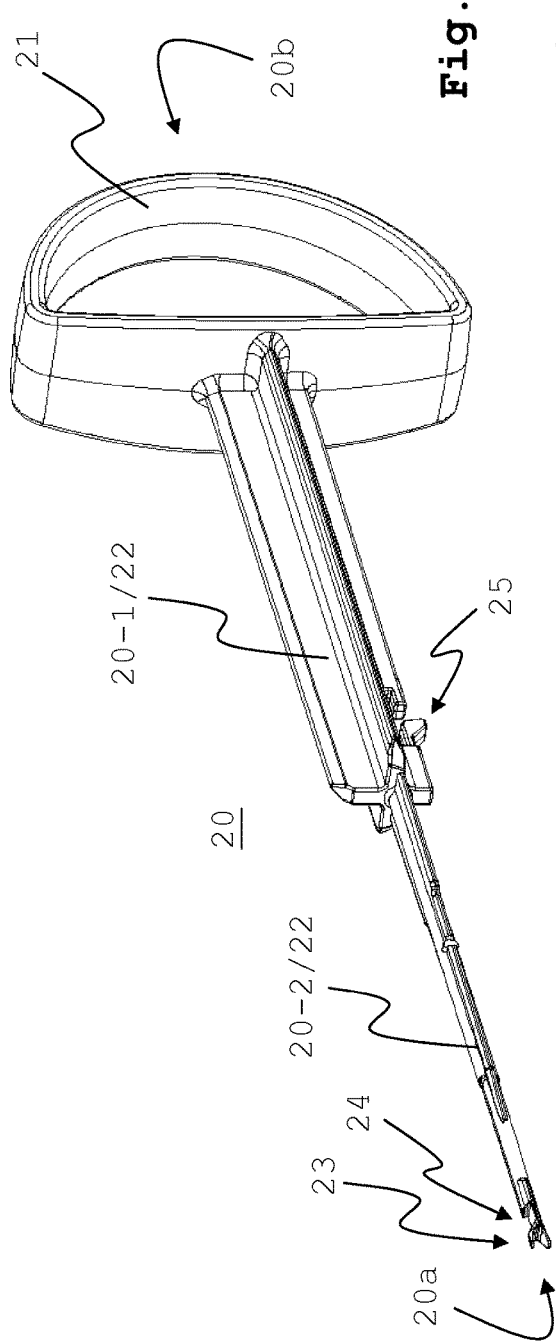
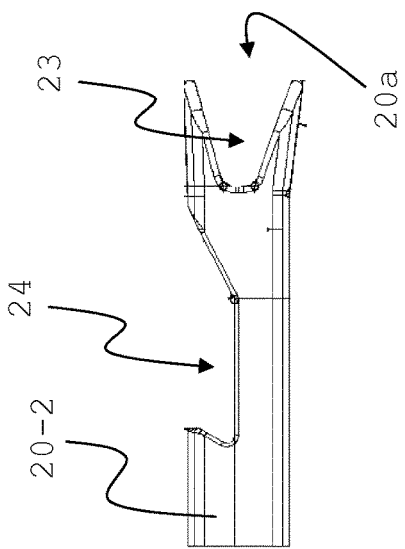
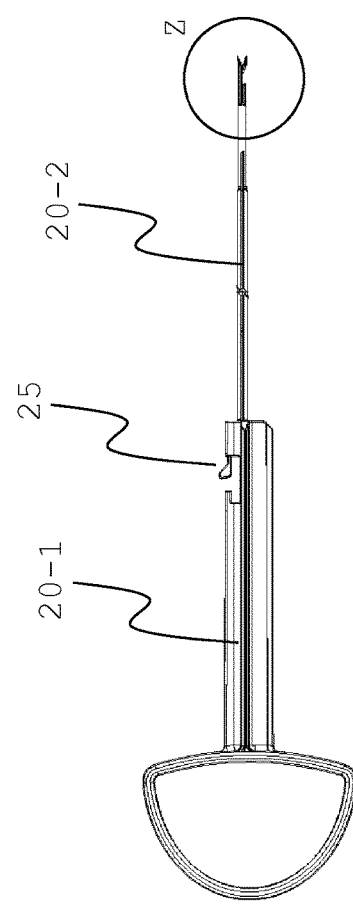
Fig. 7.a
Fig. 7.c
Fig. 7.b

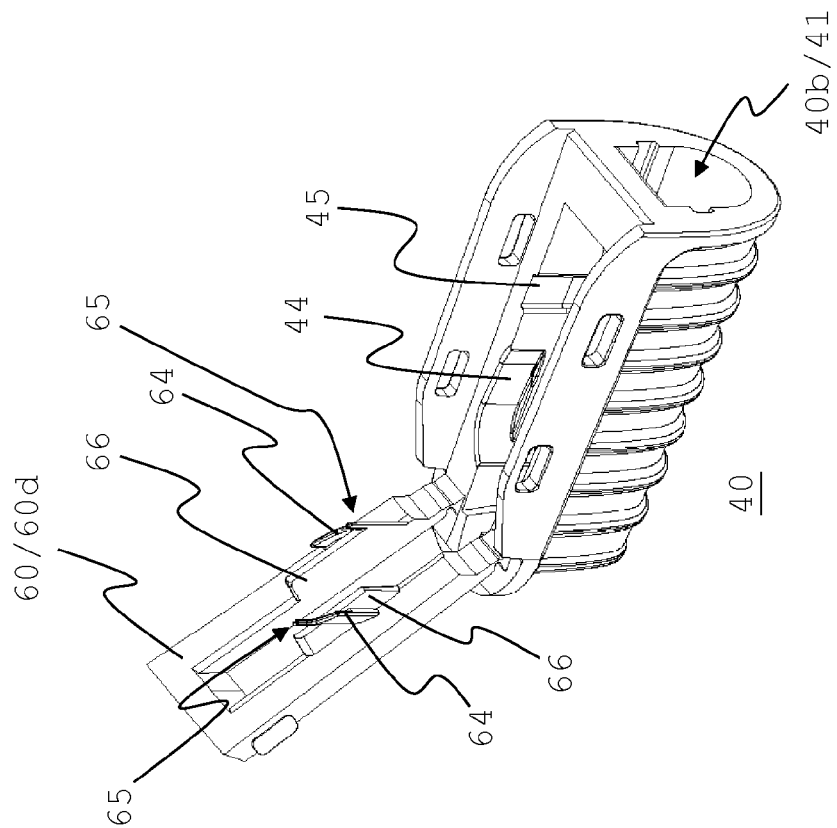
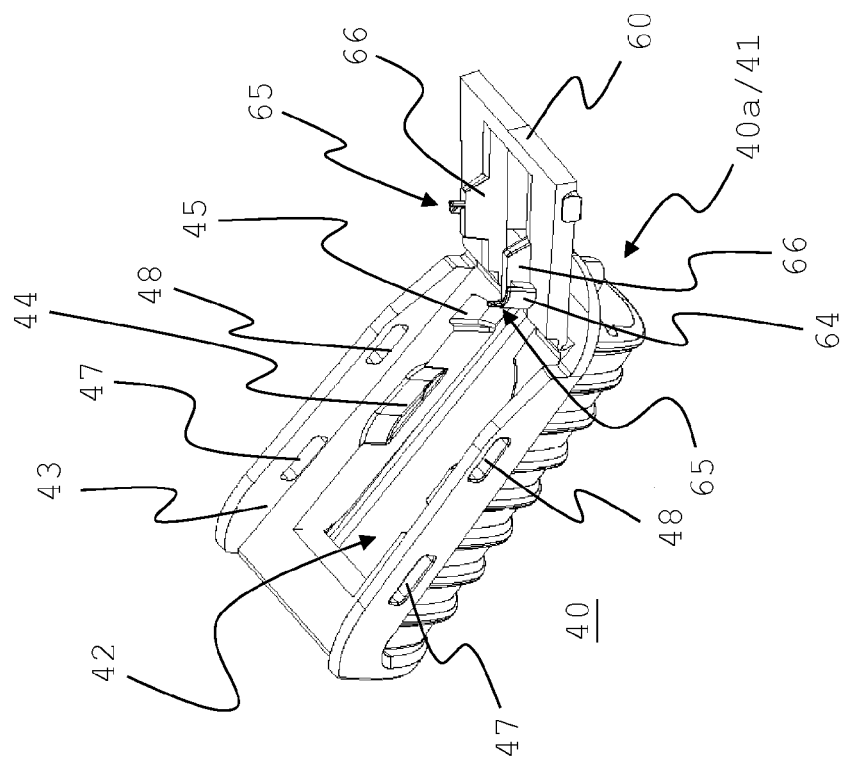

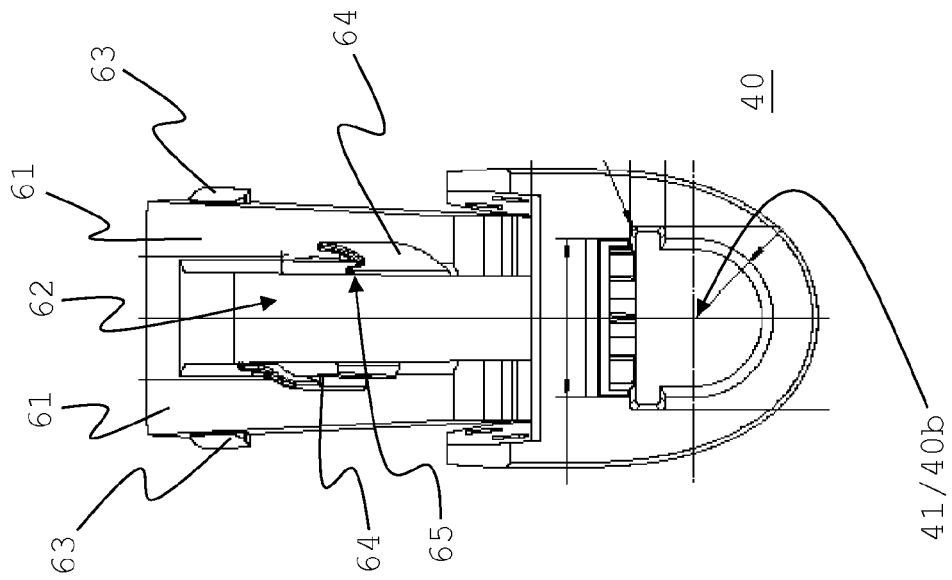
Fig. 8.d
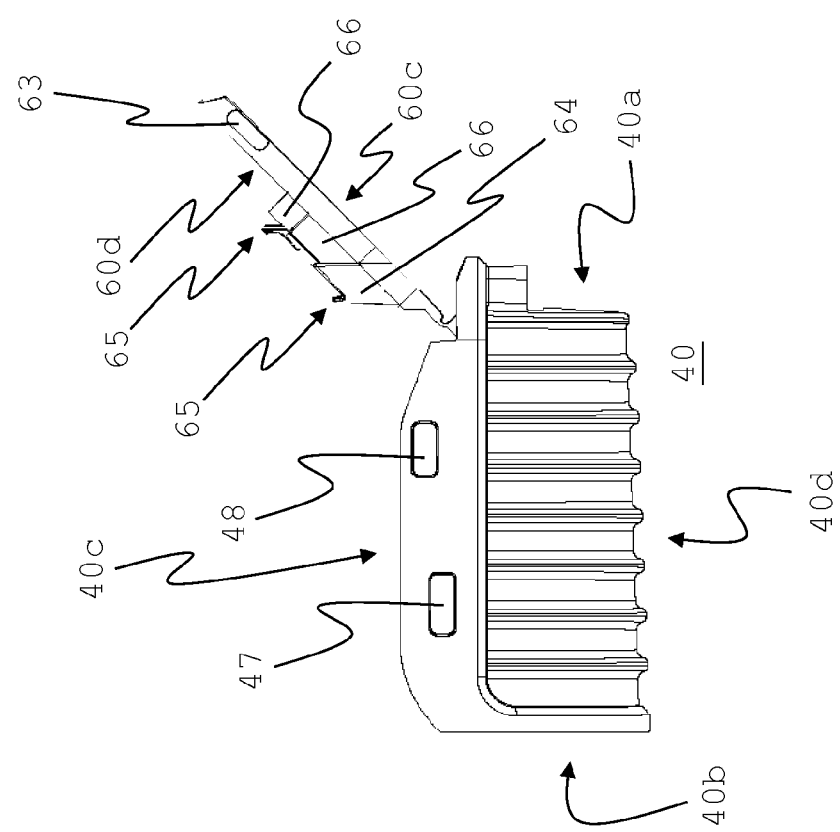
Fig. 8.c

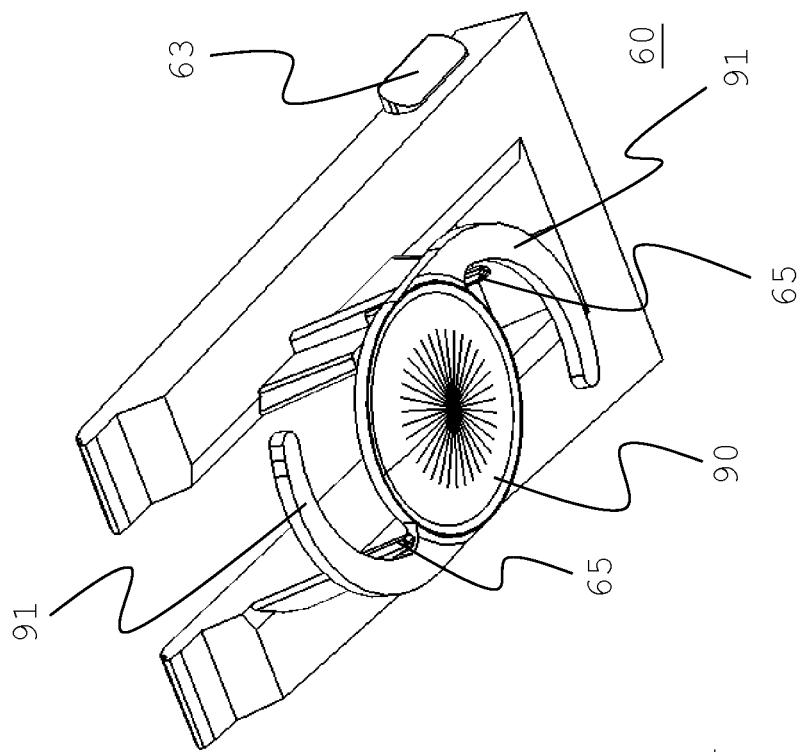
Fig. 8.f
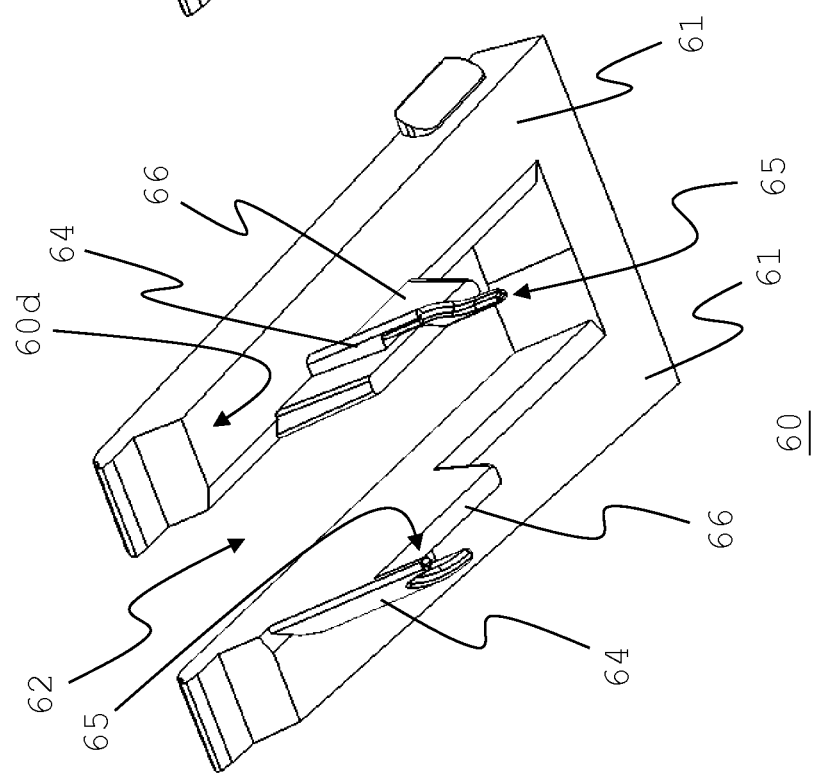
Fig. 8.e

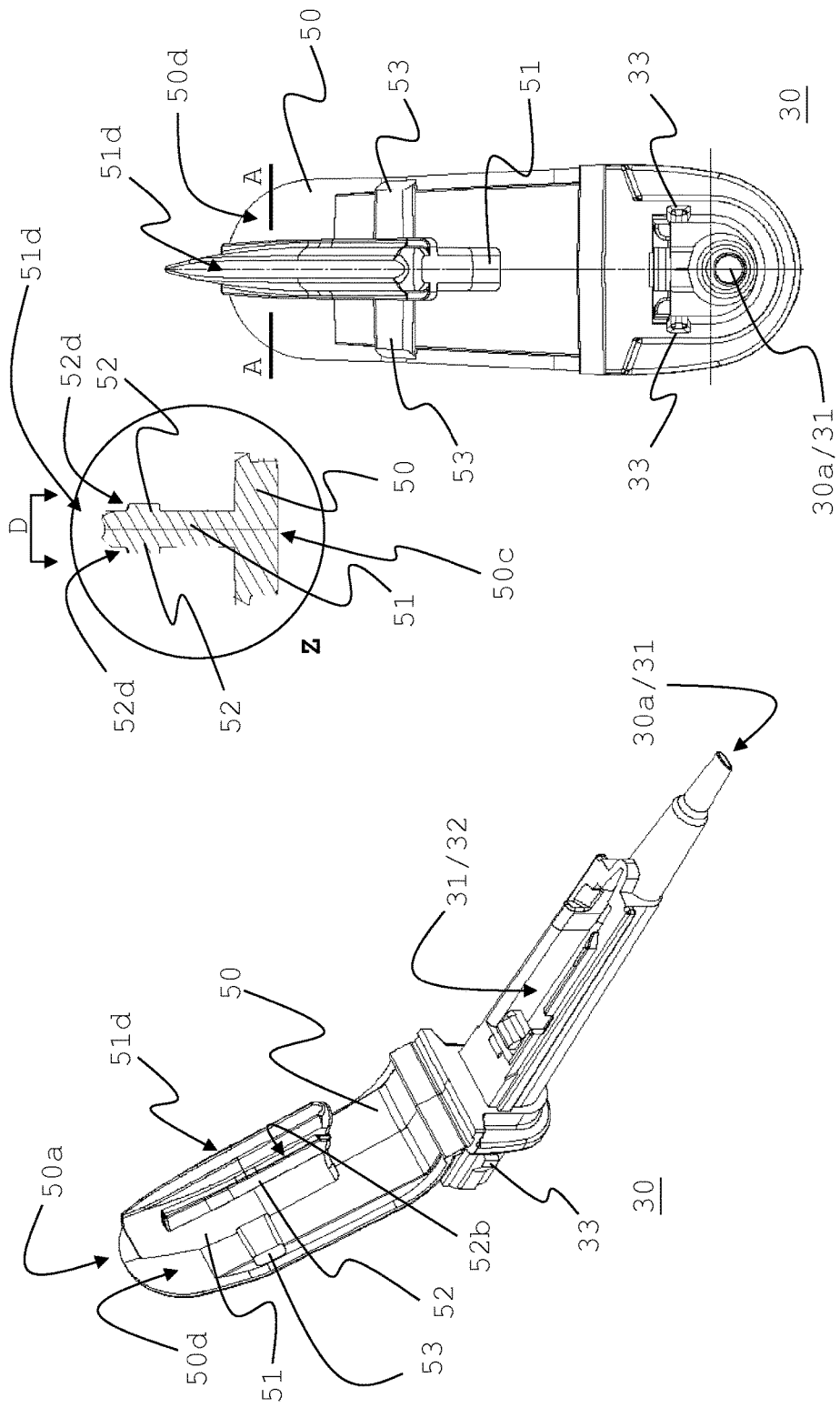

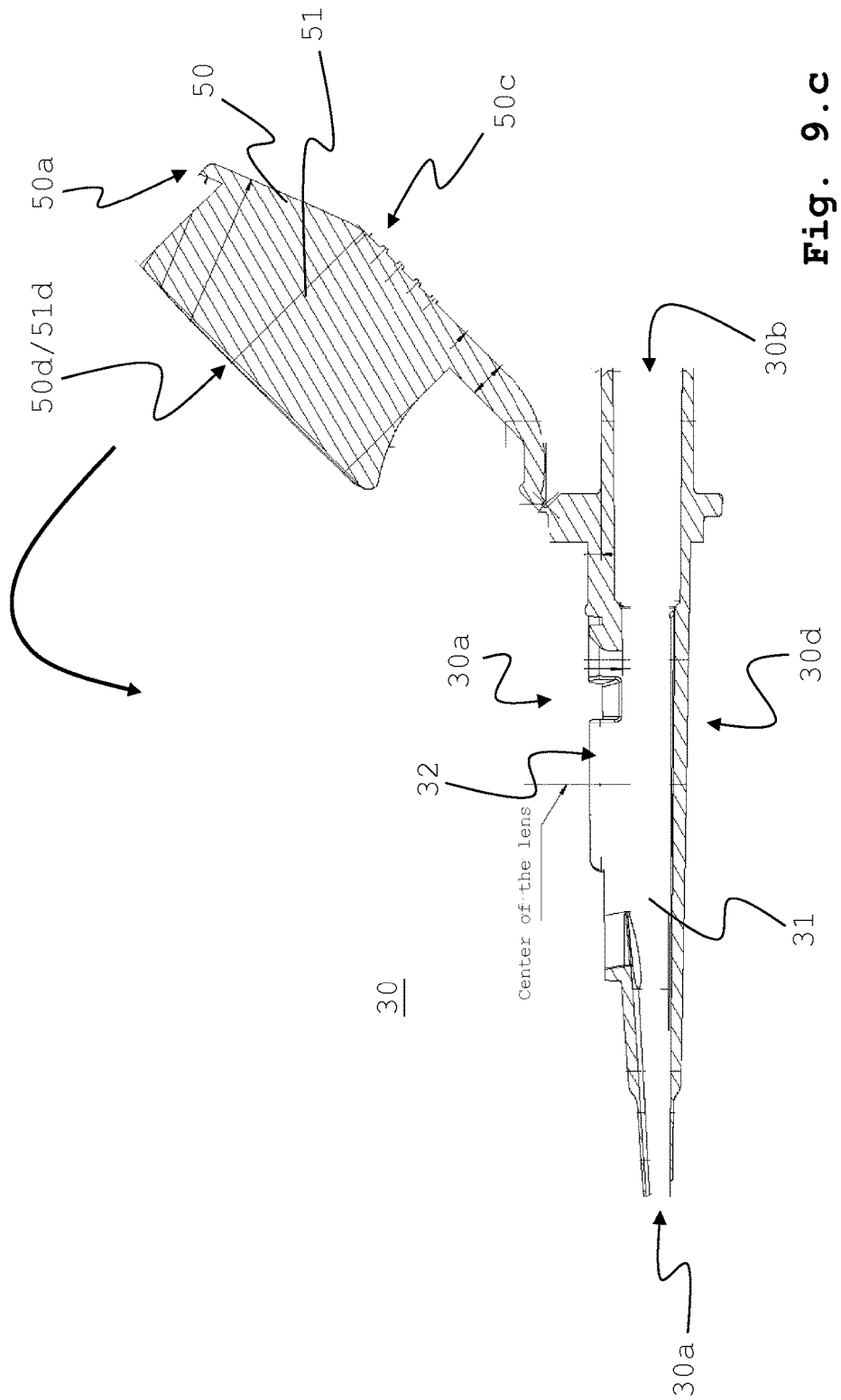
Fig. 9.c

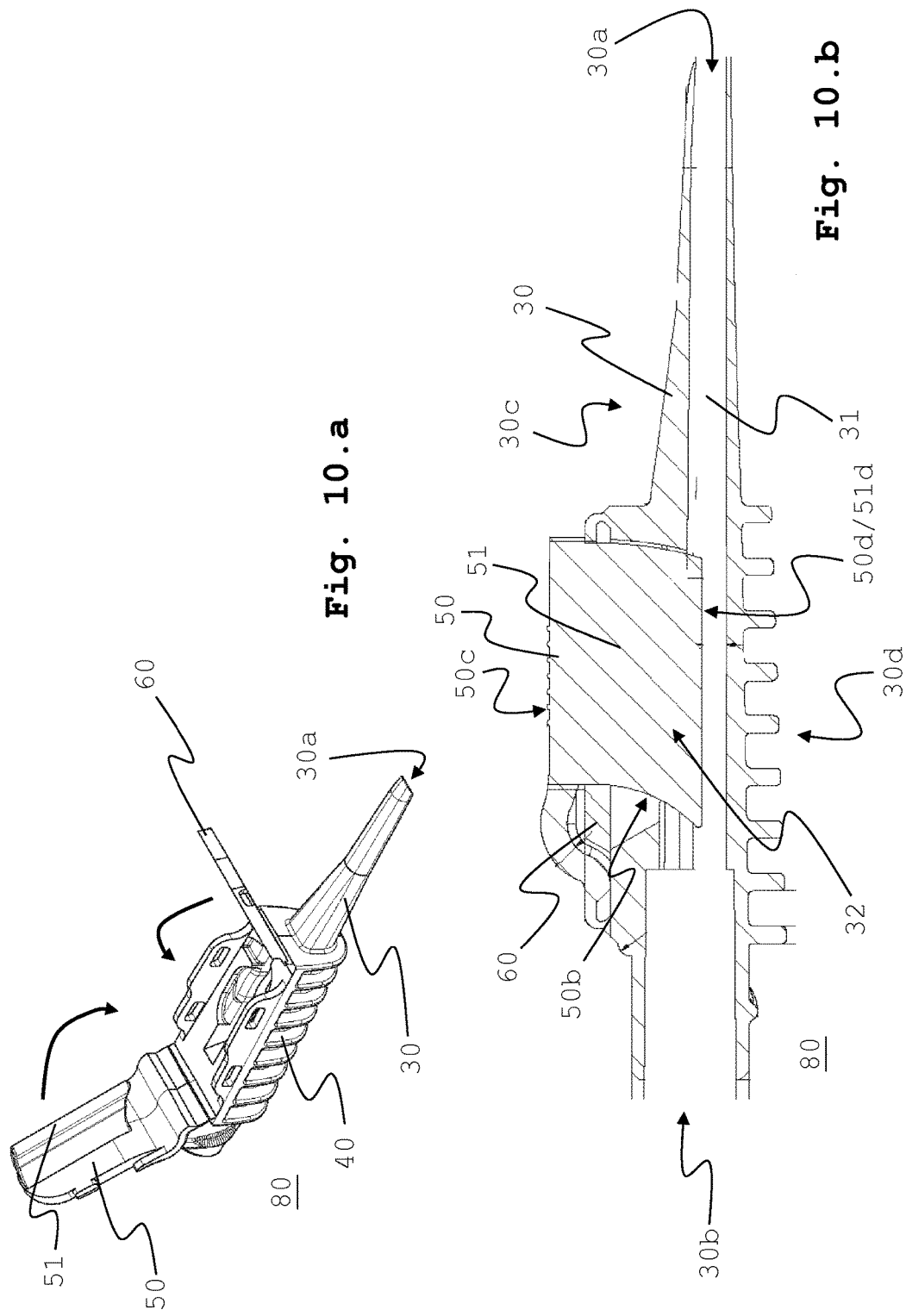

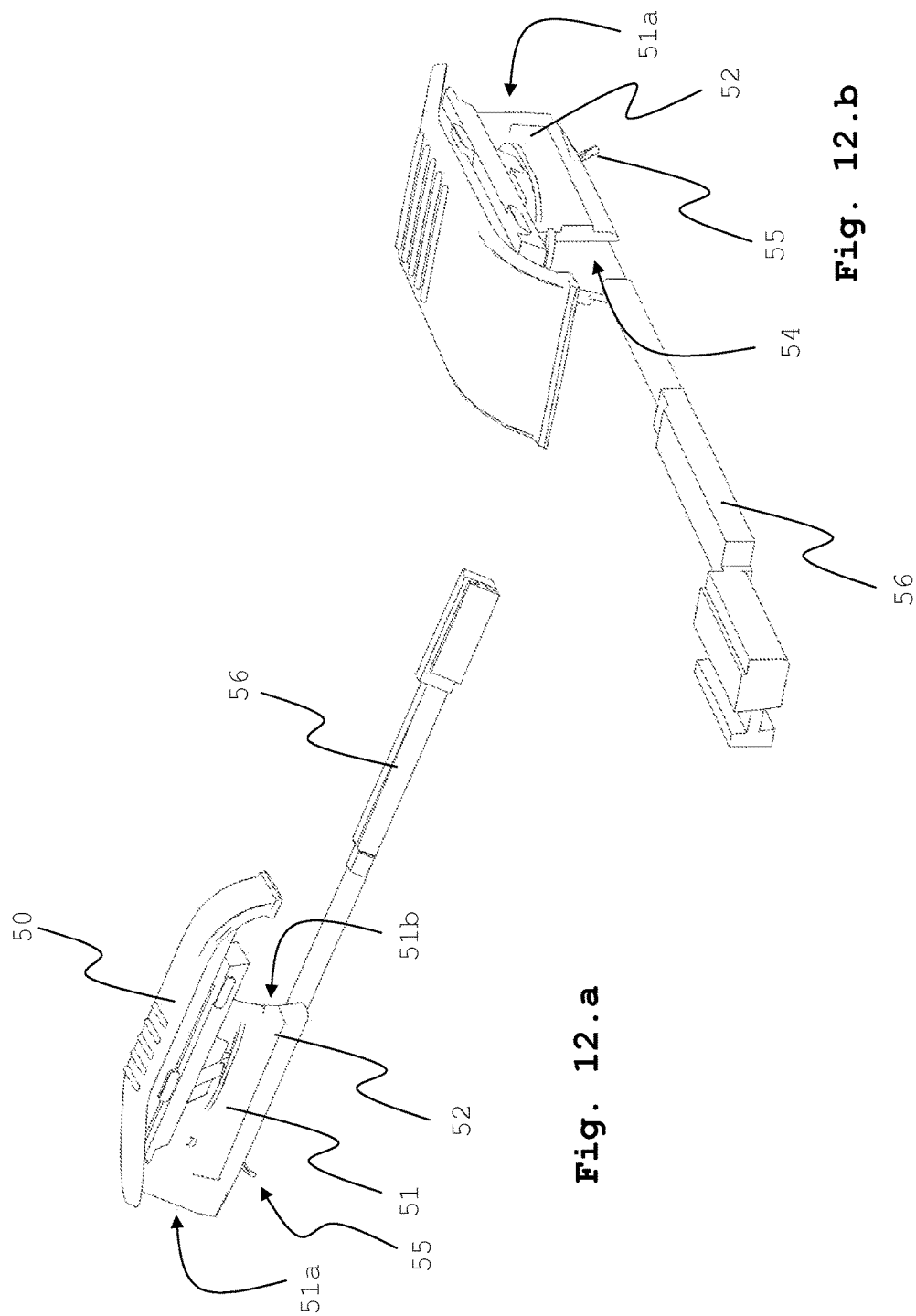

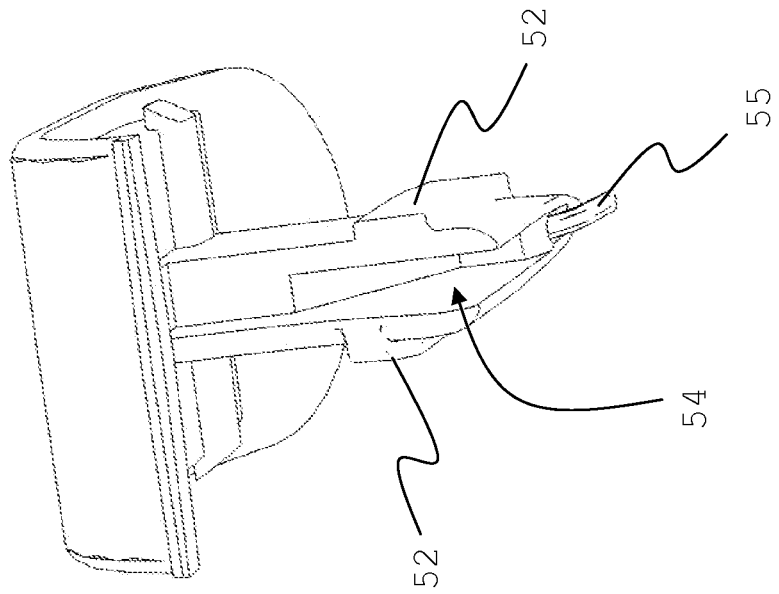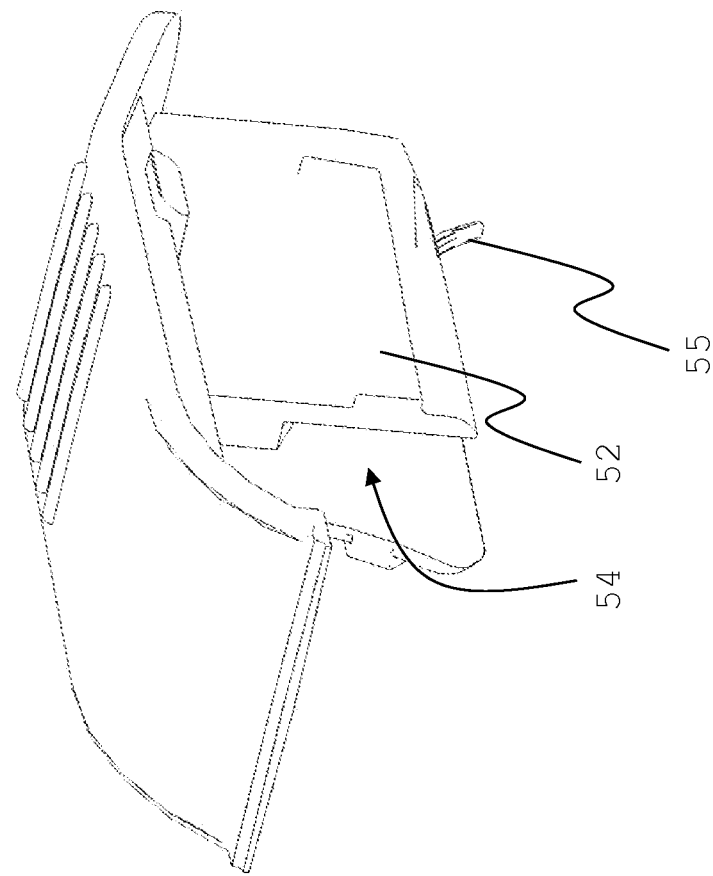

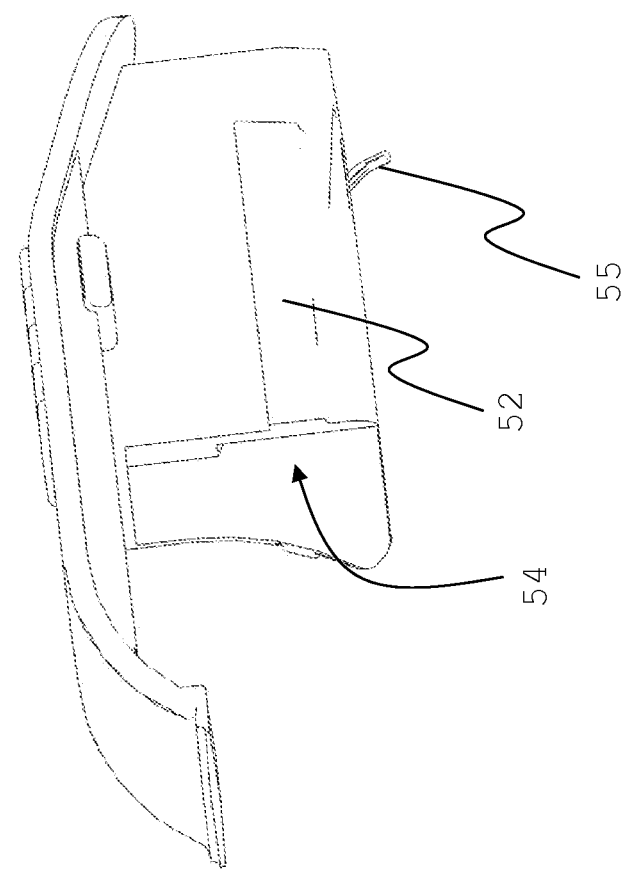
Fig. 13.d
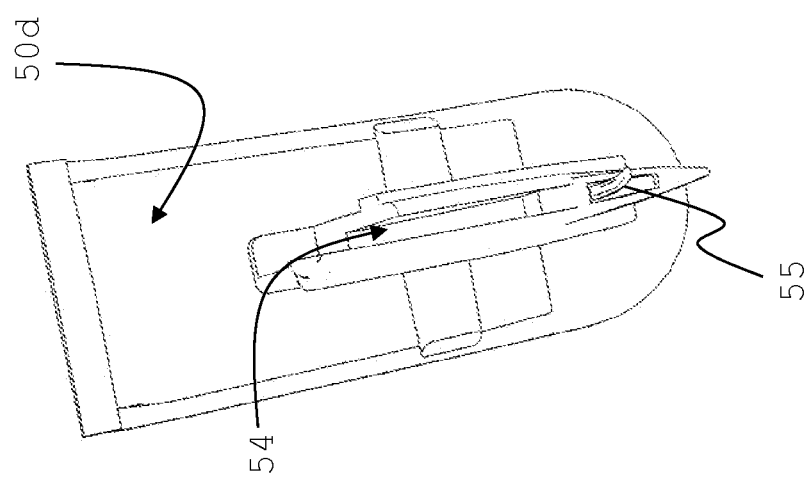
Fig. 13.c

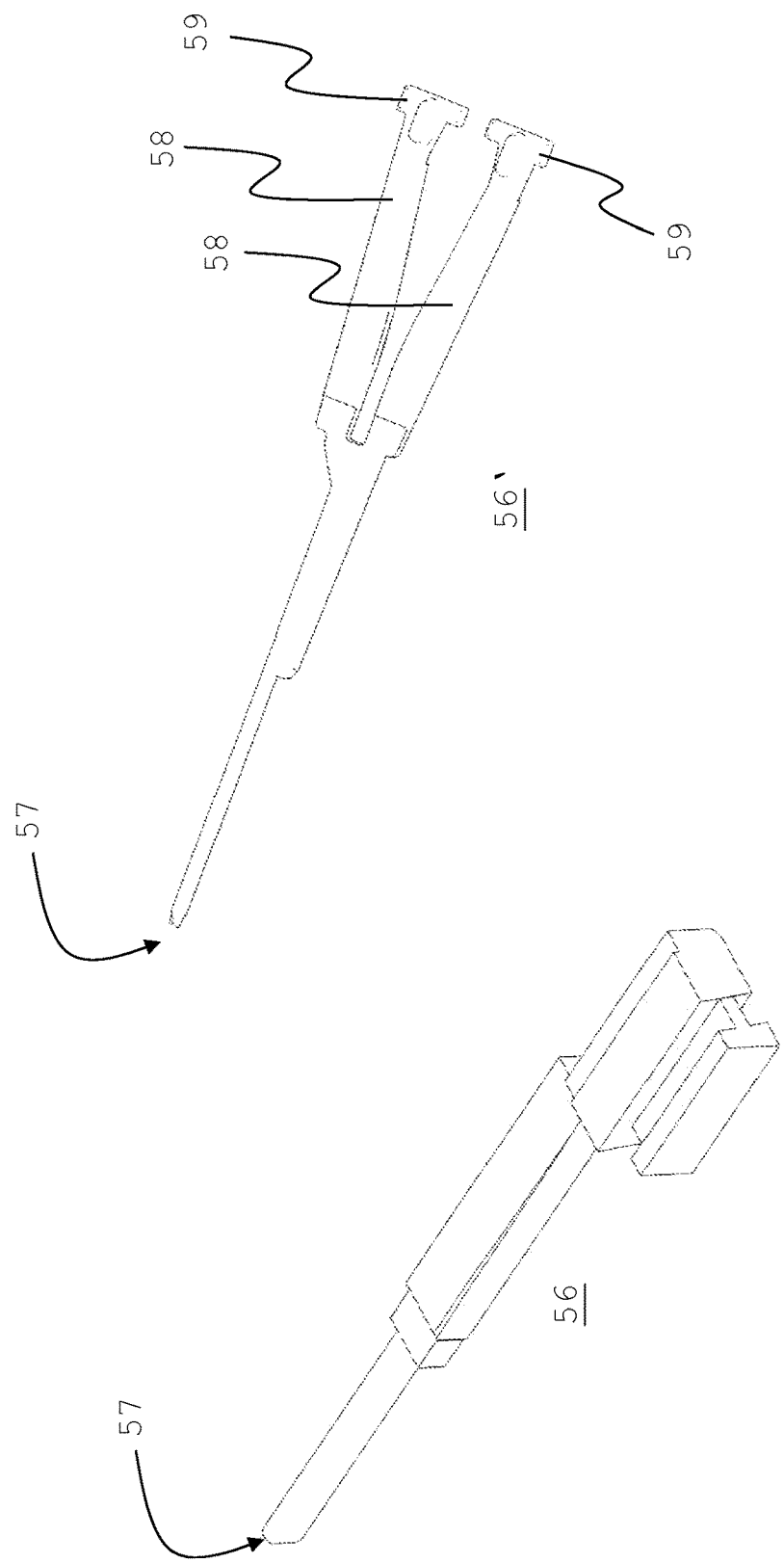

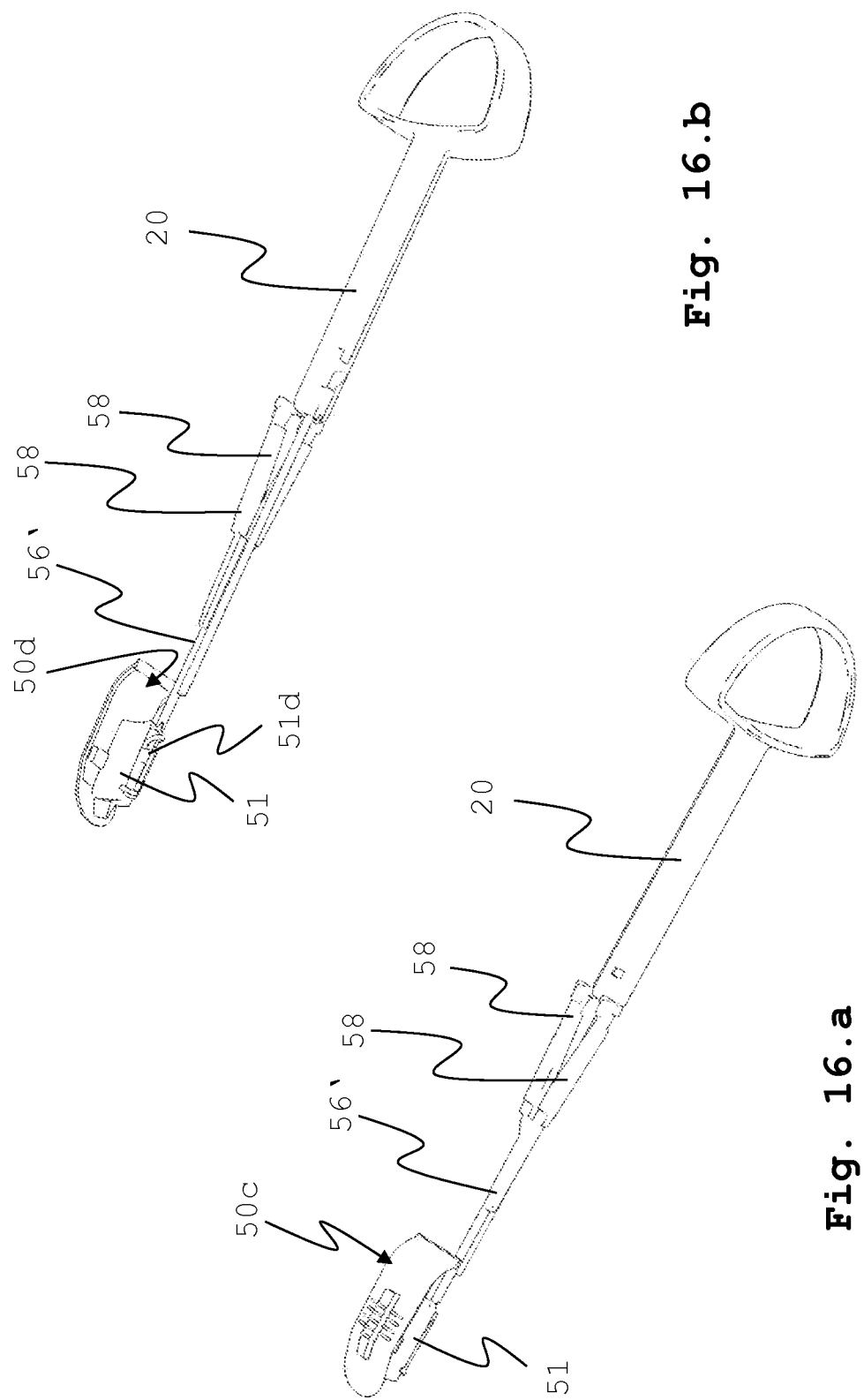

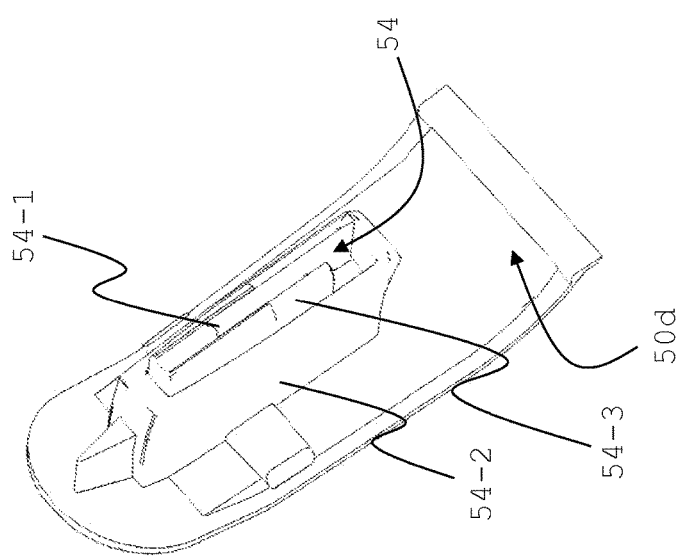
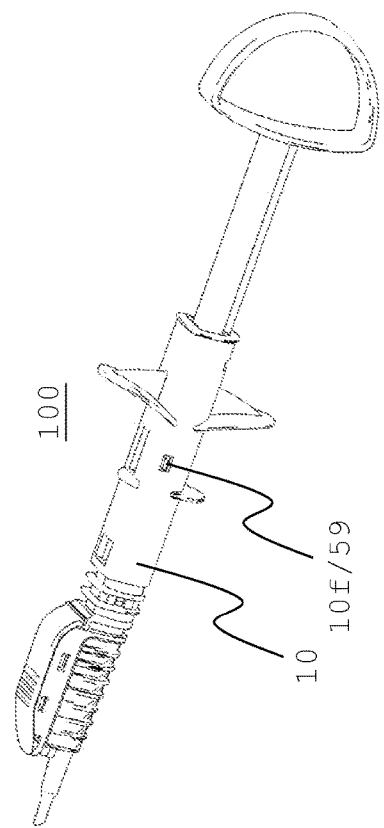
Fig. 18
Fig. 17

INJECTOR FOR IMPLANTING AN INTRAOCULAR LENS

CROSS REFERENCE TO RELATED APPLICATIONS

This application is a National Stage of International Application No. PCT/DE2012/000501 filed on May 15, 2012, which claims priority to German Application No. 10 2011 101 940.9 filed on May 18, 2011, the contents of which are hereby incorporated by reference in their entirety.

DESCRIPTION OF THE INVENTION

The present invention relates to an injector system for implanting an intraocular lens into an eye, and to a magazine for the injector system.

BACKGROUND OF THE INVENTION

Intraocular lenses are lens implants or artificial lenses to replace the natural lenses of a human eye. They are in particular used to replace the lenses of an eye affected by cloudiness (cataract) of the lens. By surgery, the affected lenses are removed and the intraocular lenses are inserted. Insertion into the eye is accomplished by means of a so-called injector, for example. It is important in this context that the surgical incision through which an intraocular lens is implanted is as small as possible (e.g. about 3 mm). This provides for the fastest possible healing process without complication and possibly also avoids the need for suture.

To be able to implant intraocular lenses which generally have a diameter of about 5 to 6 mm, the lenses must be foldable so as to fit through the small incision of about 3 mm. An injector for folding and inserting a folded lens into a human eye is described in International patent application WO 00/45746 A1, for example. The content of this patent application is fully incorporated into the present patent application by reference.

An injector is described therein for implanting and inserting a temporarily folded intraocular lens, which injector can be used to insert the folded lens into the capsula of the lens of the eye through an incision of the required size of about 3 mm in the eye.

The injector comprises a body having a thicker insertion and holding part and a thinner injection tube on an injection side and a continuous axial opening as a transport channel. In addition, the injector comprises a slider arranged so as to be displaceable axially in the transport channel. Furthermore, the injector comprises a radial insertion opening in the insertion and holding part transversely relative to the axis of the transport channel, as an insertion channel for the lens. The insertion opening communicates with the continuous transport opening. In the insertion opening, the non-folded lens rests flat on a support surface for being transported and is retained by a retaining rib extending longitudinally and centrally to the lens. The retaining rib is a plate-shaped, radially extending folding rib which can be pressed radially into the transport channel, through the insertion opening, whereby the lens is completely inserted into the transport channel folded around the retaining rib.

The injector described therein ensures safe implantation of an intraocular lens into a human and/or animal eye. The loading of the injector or the insertion of the intraocular lens into the injector can only be done just before surgery, by the operating ophthalmologist or a supportive surgical nurse.

However, in order to be able to accurately insert the intraocular lens into the eye, it is necessary for the lens to be positioned as accurately as possible on the support surface so that the lens is precisely insertable into the transport channel by means of the folding rib.

If the lens is not loaded sufficiently precisely, this may result in an undesired rotation of the lens when the lens is folded and inserted into the transport channel by means of the folding rib. Under certain circumstances, the lens may even be clamped between the folding rib and the transport channel so as to become unusable.

Therefore, the loading done by the ophthalmologist or surgical nurse presents a potential risk. Moreover, the lens previously stored in a package under sterile conditions may be contaminated when being removed from the package and placed in the injector.

GENERAL DESCRIPTION OF THE INVENTION

Against this background described above, an object of the present invention is to provide an injector for intraocular lenses that at least mitigates or even completely eliminates the drawbacks mentioned above.

It should be possible to ensure a reproducible inserting and folding of the lens in the transport channel and a reproducible inserting and unfolding of the lens in the eye, in particular even when the lens has been loaded in non-optimal manner.

These objects are already achieved by the injector system according to the independent claim. Advantageous embodiments are set forth in the dependent claims.

Generally, the invention proposes to improve the injector described in the prior art in a manner so that the securing of the intraocular lens in the injector on the one hand and the folding and inserting of the intraocular lens into the injector on the other hand is not effected by the same component.

In detail, the present invention provides an injector or injector system for inserting or implanting a lens into an eye, comprising the following components:
  an injector body having a front end and a rear end;
  a cannula arranged at the front end of the injector body, which provides a transport channel for a lens to be implanted, wherein a lens can be fed into the transport channel via a preferably lateral inlet opening;
  a magazine having a receptacle area for at least one lens which can be secured in the receptacle area by means of a retainer, wherein the magazine is arranged in a manner so that a lens can be fed into the transport channel via the preferably lateral inlet opening;
  a folding body which is insertable into the magazine and into the inlet opening, for pushing the lens into the transport channel in such a way that the lens is at least partially foldable around the folding body; and
  a slider which is slideably arranged in the injector body, preferably axially, and which can be pushed into the transport channel via the front end of the injector body in such a way that the lens can be ejected from the transport channel.

The cannula is a tube or comprises a tube, which is at least partially introduced into an eye and through which the lens is inserted into the eye. For this purpose, the lens is transferred from its initial position in the magazine into the cannula or into the transport channel of the cannula and hence to the transport position. From the transport position the lens is pushed, by means of the slider, from the transport channel through the outlet opening into the eye. The slider for ejecting the lens out of the injector may also be referred to as a lens slider. The transport channel therefore describes at least that portion of the injector through which the lens is moved by the slider. The cannula may be directly or indirectly connected to the injector body. The inlet opening or insertion opening is preferably arranged at a lateral side of the transport channel, for example at the top or bottom of the transport channel.

The lens is transferred from the magazine into the transport channel by means of the folding body, in particular by pushing or pressing. The folding body is a device for folding the lens and/or for pushing the lens into the transport channel. Preferably, the folding body is a folding plate which may also be referred to as a folding blade. The folding plate or folding body is a plate or a body configured and/or engaging the lens in a manner so that the lens is folded around the folding plate or folding body when engaged by the folding plate or folding body. The folding plate or folding body is also referred to as a folding rib, in particular if arranged on a flap. The folding body or folding plate or folding rib can be pressed into the transport channel, preferably radially.

The folding body or folding plate may be provided as a separate component, or may be combined with the injector system, preferably with the cannula. In one embodiment, the folding body or folding plate is arranged at a lower side of a flap which is preferably pivotally attached to the cannula, so that in a hinged-down condition of the flap, a lens is disposed in the transport channel and is folded around the folding body or folding plate, at least partially. In this embodiment, the flap is also referred to as a folding flap briefly, since it carries the folding plate or folding body.

In one embodiment, at least two retaining ledges for a lens are arranged at the folding body or folding plate and/or in the upper region of the transport channel, which retaining ledges define an engagement surface at least for a portion of an edge of the lens or of a periphery of the lens when a lens is pushed into the transport channel.

Generally, an intraocular lens has two haptics. In order to assist in a reliable and safe insertion of the lens into the eye, the haptics should not protrude from the lens. Rather, the haptics should be in a defined position. In one embodiment of the invention, the haptics should fit closely to the lens. For example, they may be curled up in the lens. Depending on the orientation of the lens in the injector, one haptic will be in the front region of the injector (leading haptic), and one haptic will be in the rear region thereof (trailing haptic), for example.

In one embodiment of the invention, the folding body has a receptacle area for a haptic, preferably a trailing haptic, of the lens, into which the preferably trailing haptic of the lens can be introduced. Particularly, the receptacle area for the preferably trailing haptic of the lens is provided by a recess at one end of the folding body, preferably the rear end.

For transferring the trailing haptic into the receptacle area, one embodiment of the injector system comprises a haptic slider. In a first step, the trailing haptic of the lens may be inserted into the receptacle area in the folding body by means of the haptic slider. In a second step the lens is then ejected from the injector by the slider for the lens. When being ejected the folded lens is curled, for example, thereby also curling the trailing haptic, at least partially. The trailing haptic will then be inside the curled lens, at least partially.

However, it is also possible for the haptic slider to be coupled or couplable to the slider for the lens, so that the trailing haptic of the lens may be pushed into the receptacle area of the folding body by means of the haptic slider by moving the slider for the lens. In this manner, by a preferably single actuation of the slider, the trailing haptic may be placed or curled in defined manner and the lens may be ejected from the injector.

In a variation of the invention, the haptic slider comprises at least one bending arm at which the slider is engaged or abuts when ejecting the lens, so that the at least one bending arm is biased against an inner surface of the injector body and the haptic slider is displaceable by and together with the slider towards the front end of the injector. Preferably, the haptic slider has two bending arms. A bending arm is for example an arm which is substantially deflectable resiliently.

In particular, the at least one bending arm has at least one projection through which the bending arm is pressed (or biased) against the inner surface of the injector body. When pushing the lens slider and thus also the haptic slider towards the front end of the injector, after a certain displacement distance the at least one bending arm engages into a recess, preferably a hole, in the inner surface of the injector body. Thereby the haptic slider is decoupled from of the slider for the lens.

In a further embodiment, the haptic slider has a claw for the trailing haptic of the lens at its front end.

In order to achieve a defined position of the leading haptic with respect to the lens, the injector in particular characterized in that the folding body has a stop for a leading haptic of the lens so that when pushing out the lens by means of the slider the leading haptic comes to rest on the lens by means of the stop. It is also possible for the leading haptic to be curled up in the lens when ejecting the lens, or to just come to rest on the outer surface of the lens. Specifically, the stop for the leading haptic of the lens is provided as a preferably flexible projection on a lower end of the folding body.

In one embodiment, the folding body is comprised of two parts. A base is provided, in which a folding member is inserted, which in particular includes a receptacle area for a haptic. The retaining ledges are provided by the base. The folding member is moveably disposed in the base. This may for example be achieved by the fact that the upper side of the folding member does not abut against the base in the interior of the base. An intermediate space is provided. In addition, a flexible or elastic body may be introduced in the intermediate space, for example a foam material.

The retainer is a device for securing the lens or locking the lens in a position in the magazine or in the receptacle area of the magazine, the initial position. The retainer may be provided as a separate component or may be coupled with the injector, preferably with the magazine. In one variation of the invention, the retainer is configured as a flap which is pivotally mounted to the magazine, wherein in a closed position of the flap a lens is secured. In the case where the retainer is embodied as a flap, the retainer is also referred to as a retaining flap below.

In one embodiment, the retainer has a retaining device and/or an anti-rotation protection for a lens to be stored in the receptacle area, at the side associated with (or directed toward) the lens.

The retaining device is a safety device for securing or locking the lens in the magazine or receptacle area of the magazine, especially to prevent the lens from slipping out of position in the magazine and to prevent the lens from falling out of the magazine. The anti-rotation protection mentioned is intended to prevent the lens from twisting in the magazine or in the receptacle area of the magazine.

In one embodiment, the retaining device is configured as a preferably plate-shaped projection that extends over the periphery of a lens to be secured in the receptacle area, at least along sections thereof, and which has a curvature substantially corresponding to that of the lens. Preferably, the retaining device does not engage on the optically relevant portion of the lens. The retaining device engages in an area where the haptic is joint to the lens or merges into the lens, at least in sections thereof.

In further embodiment, the anti-rotation protection is configured as at least one pin which engages between a lens and a haptic of the lens and is preferably arranged at the retaining device.

In one embodiment of the invention, the retainer has an opening. The folding plate may be inserted into the magazine and into the inlet opening of the transport channel through the opening of the retainer.

The injector body is preferably a type of housing for the injector system. The injector system may be configured in one piece or in several parts. In a preferred embodiment of the invention, the injector body, the cannula and/or the magazine are provided by separate modules which in an assembled condition form a functional unit, the injector. The magazine and the cannula may also be provided as a single component, which is referred to as a cartridge.

The magazine provides a receptacle or a lens chamber for keeping or storing the lens, and optionally for loading the injector. In a preferred embodiment of the invention, the magazine is provided as a separate module. A lens is received in the magazine. Preferably, the magazine may be placed on the cannula or push-fit to the cannula in a manner so that at least portions of the cannula are positioned or secured to the magazine or inside the magazine. The receptacle area for the lens in the magazine is characterized by the fact that the lens is arranged or disposed therein in an essentially stress-free manner, preferably in a flat position. Preferably, the magazine has an outlet area or outlet opening which is arranged so as to be aligned with the inlet opening of the transport channel, so that by means of the folding body the lens may be pushed from the magazine through the outlet area or outlet opening into the transport channel. In this variation, the cannula may be directly inserted into the magazine which is preferably disposed in a separate container, and may be latched therewith or therein, for example, so that a functional unit is provided. Preferably, the magazine and/or the lens are stored under sterile conditions within the container.

Further within the scope of the invention is a magazine as such used for the injector system described above. It is a magazine having a receptacle area for at least one lens which may be secured in the receptacle area by means of a retainer, the retainer having a retaining device for a lens and/or an anti-rotation protection for a lens on a side thereof associated with the lens.

In one embodiment, the injector system is provided with the injector body, the slider and the cannula. In this case, the magazine is provided in a manner so that it can be push-fitted over the cannula of the injector or coupled with the cannula, so that the cannula is disposed at least partially inside the magazine or at the magazine, in particular for loading the injector system with a lens.

In another embodiment, the injector system is provided with the injector body and the slider. In this case, the magazine is provided with a cannula, so that the cartridge formed by the magazine and the cannula is connectable to the injector body for loading the injector with a lens.

The injector system described above, in particular the individual modules of the injector system assembly, is/are produced using injection molding. Preferably, a transparent plastic material is used, to enable better monitoring of the lens or a displacement of the lens in the injector system. One example is a thermoplastic material.

The injector of the invention is particularly suitable for all soft, foldable intraocular lenses. Such lenses are for example made of acrylic, silicone and/or hydrogel material. The injector of the invention is easily adaptable to different types of lenses, in particular in terms of the configuration and/or material thereof.

The specific dimensions and/or shapes of the individual modules and/or the characteristics of the injector system depend on the design of an intraocular lens to be implanted, inter alia. The injector of the invention may be used as a pre-loaded disposable or single-use injector.

Generally, the following dimensions are possible:
The injector body has a length from about 50 mm to about 70 mm and/or a diameter (without handles) from about 8 mm to about 16 mm.
The slider has a length (without handle) from about 100 mm to about 130 mm and/or a diameter from about 6 mm to about 8 mm in the first section, and from about 1 mm to about 3 mm in the second section.
The cannula has a length from about 45 mm to about 65 mm and/or a diameter from about 5 mm to about 15 mm in the area of the inlet opening. The transport channel has a diameter from about 3 mm to about 7 mm in the region of the inlet opening and/or a diameter from about 1 to 3 mm in the region of the outlet opening.
The magazine has a length from about 25 mm to about 35 mm and/or a height from about 10 mm to about 20 mm and/or a width from about 5 mm to about 15 mm.

The present invention will now be described in more detail by way of the following exemplary embodiments. For this purpose, reference is made to the accompanying drawings. The same reference numerals in the individual drawings refer to the same parts.

FIGS. 1.a to 1.d show the injector of the invention in an assembled state (FIG. 1a); with the retaining flap open and the folding flap open and therefore the folding rib not inserted (FIG. 1.b); without the magazine (FIG. 1.c); and without the cannula (FIG. 1.d).

FIGS. 2.a and 2.b are perspective views illustrating the loading of the magazine with a lens, with the retaining flap open (FIG. 2.a), and closed (FIG. 2.b).

FIGS. 3.a to 3.d are perspective external views illustrating the loading of the injector (FIGS. 3.a to 3.c), and the unlocking of the injector (FIG. 3.d).

FIGS. 4.a to 4.c are perspective internal views illustrating the loading of the magazine (FIG. 4.a), the unlocking of the injector (FIG. 4.b), and the ejection of the lens from the injector (FIG. 4.c).

FIGS. 5.a and 5.b show, in a perspective view, the lens arranged in its non-folded state in its initial position in the magazine (FIG. 5.a), and in its folded state in the cannula (FIG. 5.b).

FIGS. 6.a to 6.c show details of the housing, in a perspective external view (FIG. 6.a), in a cross-sectional view (FIG. 6.b), and in an elevational view of the rear end (FIG. 6.c).

FIGS. 7.a to 7.c show details of the slider, in a perspective view (FIG. 7.a), in a side view (FIG. 7.b), and in an enlarged side view of the tip (FIG. 7.c) thereof.

FIGS. 8.a to 8.f show details of the magazine, in a perspective view (FIGS. 8.a and 8.b), in a side elevational view (FIG. 8.c), in a front elevational view of the magazine (FIG. 8.d), and in a perspective view to the lower surface of the retaining flap (FIGS. 8.e and 8.f), with the lens.

FIGS. 9.a to 9.c show details of the cannula, in a perspective view (FIG. 9.a), in a front elevational view (FIG. 9.b), and in a cross-sectional view (FIG. 9.c).

FIGS. 10.a and 10.b show an alternative embodiment including a cartridge, in a perspective view (FIG. 10.a), and in a cross-sectional view (FIG. 10.b).

FIG. 11 shows a perspective view of an embodiment of the injector according to the invention with a modified folding body and a haptic slider.

FIGS. 12.a and 12.b are two side views of the modified folding body and the haptic slider of FIG. 11 without the other injector components.

FIGS. 13.a to 13.d are different views of the modified folding body of FIG. 11.

FIG. 14 illustrates a first embodiment of the haptic slider of FIGS. 11 to 12.b.

FIG. 15 illustrates a second embodiment of a haptic slider.

Figure 11:
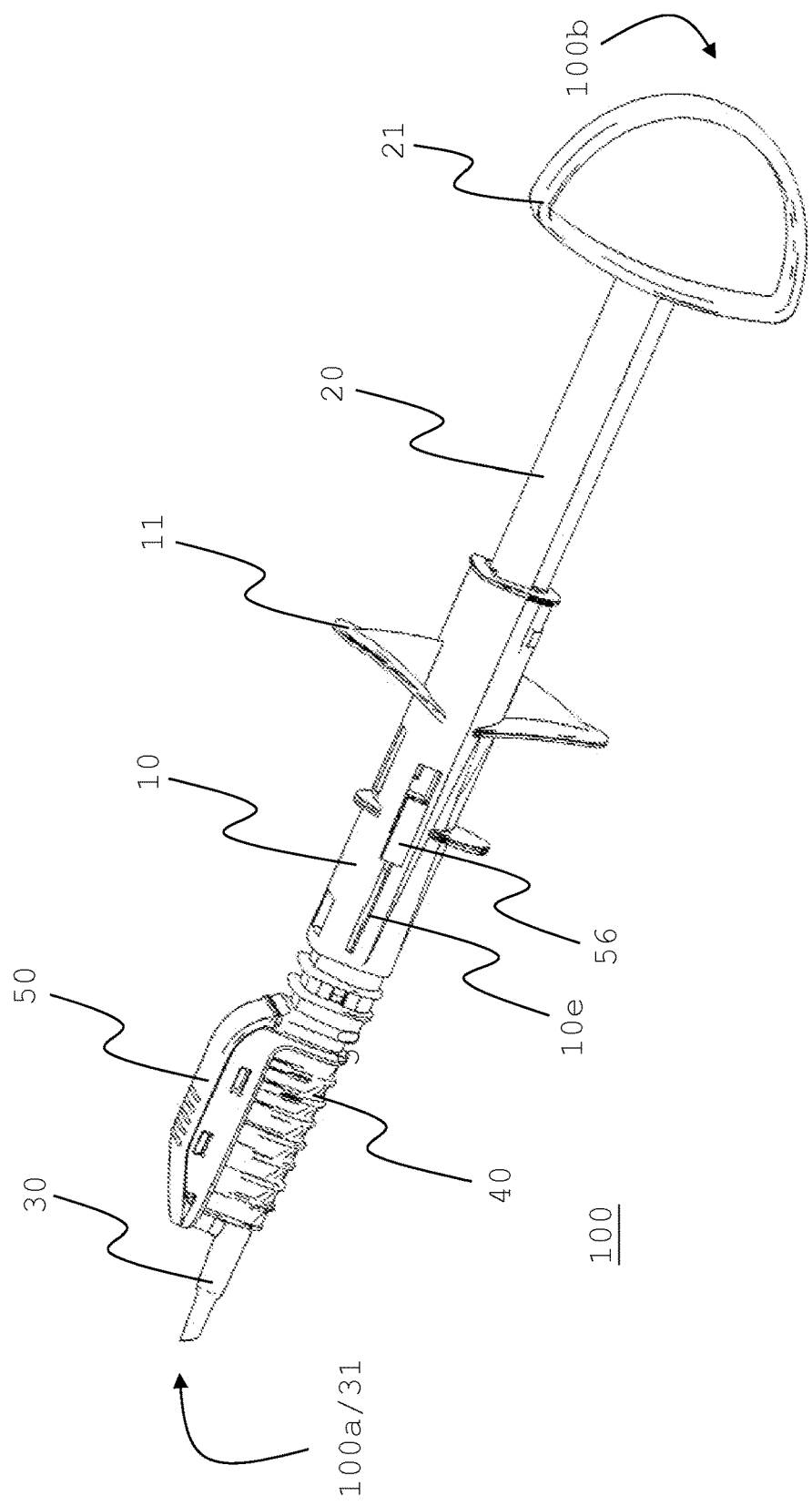

FIGS. 16.a and 16.b show the haptic slider of FIG. 15 operatively coupled to the lens slider and the folding body, in a top view (FIG. 16.a), and in a bottom view (FIG. 16.b).

FIG. 17 shows an embodiment of the injector according to the invention with the haptic slider of FIG. 15.

FIG. 18 illustrates another embodiment of a folding body having a receptacle area for the trailing haptic of a lens.

DETAILED DESCRIPTION OF THE INVENTION

The injector system 100 according to the invention will be described by way of an exemplary modular injector 100 in which the retainer 60 is formed as a flap 60 and in which the folding plate 51 is attached to a flap 50. The retainer 60 configured as a flap 60 will be referred to as a retaining flap 60 below. The flap 50 which carries the folding plate or rib 51 will be referred to as a folding flap 50 below. The injector body 10 will be referred to as a housing 10 below.

FIGS. 1.a to 1.d show an injector 100 according to the invention in its assembled state. The modules that make up the injector 100 include a housing 10, a slider 20, a cannula 30, and a magazine 40. Details of the individual modules 10 to 40 are illustrated in the subsequent FIGS. 2.a through 10.b.

FIG. 1a shows the injector 100 in its fully assembled state. Cannula 30 is arranged at the front end 10a of housing 10. Cannula 30 and housing 10 are joint to each other, for example by a snap-fit. Cannula 30 has a transport channel 31 for the lens 90, for delivering lens 90 from injector 100 and inserting lens 90 into an eye. Magazine 40 is placed, preferably plugged-on to cannula 30. Preferably, cannula 30 and magazine 40 are snap-connected to each other.

Folding flap 50 carrying folding rib 51 is positioned in its hinged-down state. Therefore, lens 90 is already located in transport channel 31 of cannula 30. The injector 100 is unlocked, so to speak. Injector 100 is ready for use. Slider 20 is inserted from the rear end 10b of housing 10. It is arranged so as to be axially slidable within housing 10. Slider 20 is disposed in housing 10 so as to exit on the front end 10a of housing 10 such that it can enter into the transport channel 31 of cannula 30. Slider 20 and transport channel 31 are adapted to each other in shape and/or size so that the slider 20 is also axially movable in the transport channel 31. By moving or pushing slider 20 towards the front end 100a of injector 100, the lens 90 which is located in the transport channel 31 of cannula 30 is ejected from the injector 100.

The front end 30a of cannula 30 or of transport channel 31 defines the outlet opening for lens 90. Slider 20 or injector 100 may be actuated by applying the index finger and the middle finger to handles 11 of housing 10 and by engaging the thumb in handle 21 of slider 20, for example. For further details about loading or equipping, locking, unlocking and/or applying injector 100 or ejecting the lens, reference is made to the description of FIGS. 2.a through 5.b.

FIG. 1.b shows the injector 100 in a non-loaded or non-equipped state. There is not yet a lens 90 in magazine 40. Magazine 40 is shown with the retaining flap 60 open. Accordingly, folding flap 50 is likewise shown in a non-hinged-down state.

It is possible for the magazine 40, for example, to only be loaded with a lens 90, when it has been placed on the injector 100 or has been attached to cannula 30. Preferably, however, magazine 40 is loaded with a lens 90 and lens 90 is secured in magazine 40 by means of retaining flap 60 before magazine 40 is mounted to the injector 100 or cannula 30.

This is particularly advantageous since the loading may be accomplished under sterile conditions, for example by a manufacturer of lenses. The loaded magazine 40 can then be stored under sterile conditions in a storage container, for example in a blister pack which is preferably filled with a sterile liquid.

Prior to an initial operation of the injector 100, first the storage container is opened. The magazine 40 may be mounted to the cannula 30 by immersing injector 100 into the storage container and attaching magazine 40 to cannula 30. This offers the advantage that sterile conditions are maintained as long as possible and that the transport channel 31 of cannula 30 is wetted with the storage liquid, so that the lens 90 and the slider 20 will slide better in the transport channel 31.

The injector 100, in particular housing 10, slider 20, cannula 30 and/or magazine 40 may also be used more than once. Preferably, however, they are used as one-way components.

In order to get a better overview of the configuration and modular nature of injector 100, FIG. 1.c shows the injector 100 without magazine 40. Preferably, the injector 100 as shown (without magazine 40) and the magazine 40 are packed separately, in particular under sterile conditions in each case, in a package for the injector and in a package for the magazine, in particular in a loaded state. Preferably, the two packages are opened just before the initial operation of the injector 100, injector 100 is taken from the package and coupled with the magazine 40 as exemplified above.

For an even better understanding, FIG. 1.d shows the injector 100 without the cannula 30. Cannula 30 and housing 10 may for example be joined or connected using a latching mechanism and/or by twist-on fitting.

In order to illustrate the operation of injector 100 and the cooperation of retaining flap 60 and folding flap 50, FIGS. 2.a through 5.b show the positioning of lens 90 in a non-folded state in magazine 40, and in a folded state in transport channel 31.

First, the two FIGS. 2.a and 2.b illustrate the loading of magazine 40. Shown is a detailed view of a magazine 40 loaded or equipped with a lens 90, with the retaining flap 60 open (FIG. 2.a), and closed (FIG. 2.b). Magazine 40 is provided by a hollow body. Inside the magazine 40 there is a cavity 41 which opens towards an upper end 40c of magazine 40 and towards a front end 40a and a rear end 40b of magazine 40, and which is confined at its lower end 40d by bottom 42 and at the lateral sides by side walls 43. Thus, an axial through-passage is defined in magazine 40 as a receptacle area for cannula 30, into which cannula 30 may be introduced (see also FIGS. 3.a and 3.b).

The interior 41 of magazine 40 provides a receptacle area 44 for the lens 90 and optionally for the haptic 91 of the lens. Receptacle area 44 for lens 90 is configured as at least one recess 44 in an inner surface of the wall 43 of magazine 40. In detail, herein, the receptacle area 44 is formed by two recesses 44 in the inner surface of wall 43 of magazine 40. The two recesses 44 are formed in the opposite walls 43 of magazine 40. Due to the view chosen, only one recess 44 is visible in FIG. 2.*a*. Recesses 44 are adapted to the shape and size of lens 90, and optionally to the haptics 91 thereof. Preferably, the recesses are curved, at least in sections thereof. Lens 90 and/or haptics 91 rest(s) at least partially on the bottom of the respective recess 44. The bottom of recess 44 is located above transport channel 31 and below the upper end 40*c* of the magazine.

Especially in order to prevent the haptics 91 from twisting or jamming, two guiding areas 45 are additionally provided for the haptics 91, which are formed as recesses 45 or as a channel 45 in the inner surface of wall 43 of magazine 40. They do not have a bottom herein, they extend until the through-passage into which the cannula 30 or transport channel 31 is inserted. The guiding and/or receptacle areas 45 for haptics 91 are arranged offset from receptacle areas 44 along the longitudinal axis of magazine 40.

In order to provide for a safe transfer of the lens 90 in magazine 40 and to prevent the lens 90 from dropping out, for example, retaining flap 60 is provided. Retaining flap 60 has been chosen to be substantially U-shaped herein. Retaining flap 60 has two legs 61 and an opening 62 defined between legs 61. Opening 62 provides a passage region for folding flap 51. In the present example, retaining flap 60 is coupled with magazine 40. It is pivotally connected to magazine 40. Retaining flap 60 is joined to magazine 40 through the pair of legs 61. Preferably, retaining flap 60 and magazine 40 are integrally formed. An appropriately sized thin joint between retaining flap 60 and magazine 40 forms some kind of a hinge between retaining flap 60 and magazine 40. By hinging down retaining flap 60, lens 90 is secured in its position in magazine 40 (see FIG. 2.*b*). For the purposes of illustration, FIG. 2*b* shows retaining flap 60 both in its open and in its closed position.

The means for positioning and locking lens 90 are arranged at the lower surface 60*d* of retaining flap 60 (see FIG. 2.*a*). These include a retaining device 64 and an anti-rotation protection 65. For further details about these means, reference is made to the description of FIGS. 4.*a* and 8.*a* through 8.*f*.

The means for locking retaining flap 60 and magazine 40 in the hinged-down position of the retaining flap 60 are essentially based on a latching mechanism. For this purpose, preferably, a pair of projections 63 is provided at the outer surface of retaining flap 60, which in a hinged-down state engage in a pair of corresponding recesses 47 or openings 47 in magazine wall 43 (see FIG. 2.*b*). Projections 63 of retaining flap 60 are latched in the openings 47 of magazine 40. Another pair of openings 48 is arranged laterally offset from openings 47. They are part of the fastening or locking means for folding rib 51. For this purpose reference is made to the description of FIG. 3.*d*.

FIGS. 3.*a* to 3.*d* illustrate the loading of injector 100. For a better overview, housing 10 and slider 20 are not shown. Magazine 40 is equipped with a lens 90. Retaining flap 60 is closed, or in its hinged-down state, and is preferably latched to magazine 40 (see FIG. 3.*a*). Lens 90 is located in receptacle areas 44 of magazine 40 and is secured therein by retaining flap 60 or the locking means. The locking means are at least provided by retaining device 64 and/or by anti-rotation protection 65. Lens 90 is in its initial position which is particularly suitable for transporting the magazine 40. Magazine 40 is provided. Securing of lens 90 by said means is illustrated, for example, in FIG. 4.*a*. There only lens 90 and retaining flap 60 are illustrated as part of the magazine 40.

In a subsequent step, magazine 40 is joined, preferably snap-connected, to injector 100, (for this see FIGS. 3.*a* and 3.*b* in combination, with the intermediate arrow). In detail, magazine 40 is plugged onto cannula 30, or cannula 30 is inserted into magazine 40. To this end, the tip or front end 30*a* of cannula 30 is introduced into magazine 40 from the rear end 40*b* of magazine 40. Magazine 40 is arranged on the cannula 30 as some kind of a collar (for this see FIG. 3.*c*). Injector 100 is now in a loaded or equipped state. Folding flap 50 with folding rib 51 is in an open or non-hinged-down state. Here, folding flap 50 is coupled with cannula 30. It is pivotally connected to cannula 30. Preferably, folding flap 50 and cannula 30 are formed integrally. An appropriately thin joint between folding flap 50 and cannula 30 forms some kind of a hinge between folding flap 50 and cannula 30.

In a next step, the injector 100 is unlocked. For this purpose, lens 90 is moved or transferred from its initial position in magazine 40 to its transport position in cannula 30 or transport channel 31. The transport position mentioned indicates the position from which lens 90 can be ejected from the injector 100 and inserted into an eye using slider 20. For this purpose, folding flap 50 is folded or pivoted towards the upper end 40*c* of magazine 40. Folding rib 51 arranged at the lower surface 50*d* of folding flap 50 passes between legs 61 of retaining flap 60 and engages into magazine 40. Folding flap 51 engages on the upper surface of lens 90 and pushes the lens out of its initial position in magazine 40 and into the transport channel 31 of cannula 30, while folding lens 90 into a U-shaped profile (for this see FIG. 4.*b* which only shows retaining flap 60, folding flap 50, and lens 90). To ensure safe folding of the lens 90 and to prevent possible slipping or jamming of lens 90, a pair of retaining ledges 52 is preferably provided at folding rib 51. Such ledges may also be disposed at the upper end of transport channel 31 in the region of inlet opening 32.

In a next step, the lens is discharged from injector 100 and introduced into an eye. By means of slider 20 the lens 90 is pushed out from injector 100 (see FIG. 4*c*). FIG. 4*c* essentially corresponds to FIG. 4.*b*. Additionally, however, slider 20 is shown. The front portion 20-2 of slider 20 is shown in detail. In order to enable to securely grasp the lens 90 using slider 20 and to discharge the lens 90 from the injector 100 in defined manner, slider 20 has guiding means 23 at its tip. These are configured as a kind of fork 23 (for this see also FIGS. 7.*a* through 7.*c*). Slider 20 is moved towards lens 90. Lens 90 is engaged by fork 23, in particular between the two prongs of fork 23. Additionally, slider 20 has a receptacle area 24 for the or one haptic 91 of the lens 90. Receptacle area 24 is formed as a recess 24 or groove 24 in arm 21 of slider 20. When lens 90 is discharged, haptic 91 will set in this recess 24. In this way, jamming and possible damage to haptic 91 can be avoided.

In order to illustrate again the change in position of lens 90 or the transfer of lens 90 from its initial position in the non-folded state to the transport position of lens 90 in its folded state, FIGS. 5.*a* and 5.*b* show magazine 40 in an open state. In FIG. 5.*a* lens 90 is disposed in its initial position. In FIG. 5.*b*, however, lens 90 is already in its transport position. For the sake of a better understanding, illustration of folding flap 50 with folding rib 51 which moves or displaces lens 90 from its initial position into its transport position, and illustration of cannula 30 have been dispensed with. Therefore, in FIG. 5.b it seems as if lens 90 rests on the bottom 42 of magazine 40. In fact, lens 90 is disposed in transport channel 31 of cannula 30 which is accommodated in the interior of magazine 40.

Folding flap 50 is connected with magazine 40, preferably snap-connected. Thus, the means for connecting folding flap 50 and magazine 40 are based on a latching mechanism. For this purpose, preferably, a pair of projections 53 is provided at the outer surface of folding flap 50, which in a folded-down state are engaged in a corresponding pair of recesses 48 or openings 48 in magazine wall 43 (see FIG. 3.d).

So far, injector 100 has been described in its entirety and its operation. In the description which follows, however, the individual modules 10, 20, 30, 40, 50, and 60 will be described, in particular with their essential structural features.

First, in FIGS. 6.a to 6.c, the housing 10 is illustrated, including handles 11 to which the fingers may be applied. Thus, the injector 100 may be operated like a syringe. Cannula 30, not shown herein, is connected to the front end 10a of housing 10. In the present example, it is connected to housing 10 by a latching mechanism. Recesses 12 are provided in housing 10 into which corresponding lugs 33 formed on cannula 30 are engaged. Slider 20, not illustrated in these figures, is inserted into the housing 10 from the rear end 10b thereof. In order to ensure precise sliding of slider 20 in housing 10, guiding means 13 are provided inside housing 10, which are in form of guiding rails 13. By way of example, rails 13 are arranged on the inner surface of the upper end 10c and on the inner surface of the bottom end 10d in this case. Hole 14 defines a final position for slider 20.

Next, slider 20 is illustrated in FIGS. 7.a to 7.c. It has a first portion 20-1 of a shape and size corresponding to the guiding rails 13 in housing 10, and in the present example it is cross-shaped. In this manner, ribs are defined to stabilize the slider 20. Towards the rear end 20b, grip 21 is arranged on first portion 20-1. First portion 20-1 has a length essentially corresponding to the length of housing 10. Towards the other end, first portion 20-1 merges into a second portion 20-2. This second portion 20-2 enters into the transport channel 31 of cannula 30 for discharging the lens 90. The shape and size of second portion 20-2 correspond to those of transport channel 31 of cannula 30, and in the present example it is cross-shaped, at least in sections thereof. So ribs are defined to stabilize the slider 20. The second portion 20-2 is tapered in cross section towards the front end 20a of slider 20. The length of the second, forward portion 20-2 is selected such that the tip of slider 20 may protrude from the transport channel when discharging lens 90. The slider 20 which may also be referred to as a plunger 20 is preferably arranged so as to be displaceable axially in both the housing 10 and the transport channel 31 in cannula 30. The final position of slider 20 during ejection of the lens 90 may, for example, be defined by the engagement of handle 21 at the rear end 10b of housing 10.

In order to enable to securely grasp the lens 90 by means of the slider 20 and to discharge the lens 90 from the injector 100 in defined manner, slider 20 has guiding means 23 at its tip or front end 20a. These are configured as a kind of fork 23. Additionally, slider 20 has a receptacle area 24 for the or one haptic 91 of lens 90. Receptacle area 24 is formed as a recess 24 in the second portion 20-2 of slider 20. Instead of fork 23, an elastic member may be used, for example a substantially cylindrical buffer, or an intermediate piece, in particular made of silicone.

When slider 20 is withdrawn from housing 10, latching lug 25 will be engaged in hole 14 in housing 10 so as to define a final position of slider 20 in the housing 10, so that the slider 20 can be prevented from falling out of the housing 10, for example.

FIGS. 8.a to 8.d illustrate the magazine 40 with the retaining flap 60 without a lens 90. FIGS. 8.e and 8.f, by contrast, only show retaining flap 60 with a lens 90 inserted, in order to be able to better illustrate the effect of retaining device 64 together with anti-rotation protection 65.

Magazine 40 is a hollow body which opens towards its ends 40a and 40b, and towards the top 40c. Magazine 40 constitutes a lens chamber and is particularly suitable for transporting and/or storing lens 90. It has a bottom 42 and side walls 43. A plurality of ribs is arranged on the outer surface of magazine 40, which extend in sections around the circumference of magazine 40, in particular to allow the magazine 40 to be gripped and hold safely.

Inside magazine 40 receptacle area 44 is provided, for lens 90, and guiding and/or receptacle area 45 for haptics 91 of lens 90, in particular for the end of the arm of haptics 91. Receptacle area 44 may accommodate a portion of lens 90 and a portion of haptic 91, preferably the neck of haptics 91 at lens 90.

Each of receptacle area 44 for lens 90 and guiding and/or receptacle area 45 for haptics 91 is provided as a pair of recesses 44 and 45, respectively, in side wall 43. The two recesses 44 for lens 90 correspond in shape and/or size to lens 90 and optionally to haptic 91. They are curved, at least in sections thereof. Also, they have a bottom in this example, on which a portion of lens 90 and, optionally, of haptic 91 may come to rest. The two recesses 44 are arranged axially offset to each other. The two recesses 45 are likewise arranged axially offset to each other.

Retaining flap 60 is arranged on magazine 40. On its upper end 40c, magazine 40 may be closed by means of retaining flap 60. Retaining flap 60 provides some kind of a lid for magazine 40. Retaining flap 60 may be closed by latching the pair of latching lugs 63 thereof in the pair of recesses 47 on magazine 40. Offset upwards towards the upper end 40c (with respect to recesses 47) there is provided another pair of recesses 48, for snap-connecting folding flap 50, not shown here.

Lens 90 is secured by flap 60 from falling out, slipping and twisting. For this purpose, means for positioning and/or locking lens 90 are provided at the lower surface 60d of retaining flap 60. Here, the means for positioning and/or locking lens 90 comprise a retaining device 64 and an anti-rotation protection 65.

Retaining device 64 is provided by a pair of plate-shaped projections 64, each one disposed on a respective leg 61 of retaining flap 60. They are curved, at least in sections thereof. The curvature is adapted to the curvature of a lens 90. The radius of the curvature is preferably such that the plate-shaped projections 64 do not substantially interfere with the optics of lens 90. Rather, they are associated with the periphery of lens 90 and here in particular the region where haptic 91 abuts lens 90. In the present example, each of the curved plate-shaped projections 64 is additionally stabilized by a support 66. Each of the two supports 66 is provided by a kind of rib on the lower surface 60d of retaining flap 60. The two supports 66 further serve to stiffen the retaining flap 60. Projection 64 may abut support 66 or may be formed integrally therewith.

Anti-rotation protection 65 is provided by a kind of lug 65 or a kind of tooth 65 at the lower surface 60d of retaining flap 60. Preferably it is provided by a pair of lugs 65, each one disposed on a respective leg 61 of retaining flap 60. In the illustrated embodiment, each of the two lugs 65 is arranged on a plate-shaped projection 64. Lugs 64 engage into the transition area between lens 90 and haptic 91.

FIGS. 9.*a* to 9.*c* show the cannula 30 according to the invention. Cannula 30 is a generally hollow body. Inside cannula 30 transport channel 31 is arranged, for transferring lens 90 into the eye. Cannula 30 or transport channel 31 opens towards the upper end 30*c*, at least in sections thereof, with opening 32. For example, transport channel 31 is substantially U-shaped, at least in the area of opening 32.

Cannula 30 is associated with (or directed toward) folding flap 50 which is pivotally arranged on cannula 30. Preferably, cannula 30 and folding flap 50 are formed integrally. Folding rib 51 is arranged at the lower surface 50*d* of folding flap 50. When being hinged down, folding rib 51 presses against the upper surface of lens 90. Folding rib 51 pushes lens 90 from its initial position in magazine 40 into the transport position in transport channel 31 while folding or curling the lens 90. When folding down folding flap 50, folding rib 51 engages into opening 32 in cannula body 31. Preferably, folding rib 51 has a shape and/or size which substantially corresponds to the shape and/or size of opening 32 in transport channel 31.

Folding rib 51 has a cross-sectional shape tapering towards the front end 50*a* of folding flap 50. The width of folding rib 51 decreases, preferably continuously, towards the front end 50*a* of folding flap 50. A kind of blade is defined at the front end of folding rib 51. The blade provides a guidance for the sliding of lens 90 in transport channel 31 and assists in folding or curling lens 90 in transport channel 31.

Above the lower edge of folding rib 51, at least one retaining ledge 52 is disposed on each side of folding rib 51. A retaining ledge 52 is formed as a kind of land or bar on folding rib 51, which preferably does not extend until the front end of folding rib 51 (see for example FIG. 9.*a*).

Retaining ledges 52, with their lower surfaces 52*d*, provide an engagement surface for lens 90 or the edge of the lens. The distance D between the lower surface 52*d* of one retaining ledge 52 to the lower surface of the opposite retaining ledge 52 preferably substantially corresponds to the diameter of lens 90. For example, the length D is approximately equal to the diameter of a lens 90. In this way, when the lens 90 is inserted into the transport channel 31, which involves or is accompanied by simultaneous folding of the lens 90, slipping of the lens 90 can be prevented. Without retaining ledges 52, lens 90 could slip away sideways and could be jammed.

The lower end 51*d* of folding rib 51 has a groove (see the enlarged cross-sectional view Z along axis A-A in FIG. 9.*b*). In the illustrated embodiment, lower end 51*d* is concave, at least in sections thereof. This allows the lens 90 to be better gripped by folding rib 51 when being introduced into transport channel 31.

The front end 30*a* of cannula 30 or the tip of transport channel 31 is chamfered herein, by way of example. In this manner, safe delivery of lens 90 from channel 31 may be promoted.

Cannula 30 is coupled to housing 10 at its rear end 30*b*. For this purpose, the latching lugs 33 are provided at the cannula 30, which engage in recesses 12 formed in the housing 10, preferably by being latched therein.

FIGS. 10.*a* and 10.*b* show an alternative embodiment with a cartridge 80. In this embodiment, magazine 40 and cannula 30 are not provided by two separate modules, which are combined into a functional unit by being joined. Magazine 40 and cannula 30 are provided by a single component which is referred to as a cartridge 80 here.

By the example of cartridge 80, in particular by way of the cross-sectional view of FIG. 10.*b*, the operation of the injector 100 according to the invention may again be described, in particular the function of retaining flap 60 and folding flap 50 including folding rib 51. This description may also be applied to the modular structure in particular shown in FIGS. 8.*a* through 9.*c*. For the same or similar components, reference is made to the above description of magazine 40 and cannula 30, to avoid repetitions.

Lens 90 is first secured in cartridge 80 by means of the folded-down retaining flap 60. Lens 90 is in its initial position, in particular substantially above transport channel 31. When folding down folding flap 50, folding flap 50 with its lower end 50*d* will contact the upper end 40*c* of magazine 40 and/or the upper surface 60*c* of retaining flap 60, at least sections thereof. At the lower surface 50*d* of folding flap 50, folding rib 51 is disposed, which will pass through the opening 62 in retaining flap 60 to engage into magazine 40 and to push lens 90 downwards, into the transport channel 31 of cartridge 80. Cartridge 80 is illustrated in an unlocked state. The injector 100 is ready for use. By actuating slider 20, lens 90 may be pushed out of transport channel 31. The apex of folding rib 50 is located below the upper end of transport channel 31. Thereby, the risk of a possible jamming of lens 90 in transport channel 31 is avoided.

Further, FIGS. 11 to 14 present another embodiment of the injector 100. This embodiment includes a folding body 51 having a receptacle area 54 for the trailing haptic 91 of lens 90 and a stop 55 for the leading haptic 91 of lens 90. The trailing haptic 91 of lens 90 and the associated receptacle area 54 are located toward the rear end 100*b* of injector 100. The leading haptic 91 and the stop 55 are located toward the front end 100*a* of injector 100.

First, FIG. 11 shows the injector 100 in an outer view. The modifications in folding body 51 are not visible in this view of the injector 100 (for this see the subsequent figures). What can be seen is the actuator of haptic slider 56, for which injector body 10 has an opening 10*e* in a lateral side thereof, which is formed as a slot here, through which the actuator of haptic slider 56 extends. By moving haptic slider 56 towards the front end 100*a* of injector 100, the trailing haptic 91 can be inserted into the receptacle area 54 of folding body 51.

For a better understanding, FIGS. 12.*a* and 12.*b* show the folding body 51 and haptic slider 56 alone, in two side views, without the other components of the injector. For the sake of clarity, lens 90 with its haptics 91 is not illustrated. As to the configuration of haptic slider 56, reference is made to the description of FIG. 14.

In FIG. 12.*b*, the receptacle area 54 for the trailing haptic 91 of lens 90 can be seen. Stop 55 for the leading haptic 91 of lens 90 is visible both in FIG. 12.*a* and FIG. 12.*b*. FIGS. 13.*a* to 13.*d* show the "enhanced" folding body 51 is from different perspectives.

Receptacle area 54 for the trailing haptic 91 is configured as a recess in folding body 51. Recess 54 extends from the rear end 51*b* of folding body 51 to the lower end 51*d* thereof, and extends at least partially through folding body 51. Preferably, however, it does not extend completely through the folding body 51, in particular from the rear end 51*b* to the front end 51*a*. In one embodiment, recess 54 has a depth that decreases from the rear end 51*b* of folding body 51 towards the front end 51*a* of folding body 51. It opens to the lower end 51*d* of folding body 51. The ramp formed thereby inside folding body 51 may be rectilinear or curved, for example, at least in sections thereof.

Stop 55 for leading haptic 91 is configured as a lug or a type of finger. Lug 55 is located at the lower end 51d of folding body 51. Lug 55 is preferably flexible, in particular resilient. In the illustrated embodiment, lug 55 is arc-shaped, with a curvature towards front end 51a.

By inserting folding body 51, the lens 90 is folded around the folding body 51 on the one hand, and is transferred into the transport channel 31 on the other. In order to promote safe insertion of lens 90 into an eye, it is advantageous if haptics 91 of lens 90 are arranged in a defined position.

This is achieved by receptacle area 54 associated with the trailing haptic 91, and by stop 55 associated with the leading haptic 91.

By means of haptic slider 56, trailing haptic 91 is inserted into receptacle area 54. There, the trailing haptic 91 is in a defined starting position. In a next step, slider 20 is actuated for discharging lens 90 from the injector 100. Slider 20 pushes the lens 90 forward. The trailing haptic 91 is pulled from receptacle area 54 and interposed in the folded lens 90, for example. Upon further advancement, which leads to a curling up of lens 90, trailing haptic 91 is curled into the lens 90. Thus, it will have a defined position upon ejection of lens 90.

Also upon advancement, leading haptic 91 is directed to stop 55. When further advancing lens 90, stop 55 sets or biases leading haptic 91 onto lens 90. Since stop 55 is preferably flexible, it can be pushed sideways by lens 90 upon further advancement. It is also possible for stop 55 to be disposed above lens 90 in a manner so that only the leading haptic 91 will contact it, but not the optics of lens 90 or the lens 90 itself.

Haptic slider 56 is disposed in the injector body 10 above slider 20 for lens 90. FIG. 14 shows a first embodiment of haptic slider 56. It is configured to be substantially L-shaped in this example. The short arm extends through the outer wall of injector body 10 and provides an actuating means or a type of handle for haptic slider 56. The long arm of haptic slider 56 may have a claw 57 for trailing haptic 91, not shown here. Claw 57 may be provided by a fork, for example, preferably a two-pronged fork.

Trailing haptic 91 of lens 90 may be transferred into receptacle area 54 by separately actuating haptic slider 56, or by actuating haptic slider 56 and slider 20 in combination. The embodiment of slider 56 shown in FIG. 14 is particularly suitable for separate actuation, but may also be used for being combined with slider 20.

As already stated above, a displacement of haptic slider 56 may be combined with a displacement of slider 20 for lens 90. In this case, by operating slider 20 alone, it is possible to first transfer the trailing haptic 91 of lens 90 into receptacle area 54 and then to eject lens 90 from the injector 100.

FIG. 15 shows an embodiment of haptic slider 56', which is particularly suitable for being combined with slider 20 for lens 90, which will briefly referred to as a lens slider 20 below. This embodiment may also be operated separately from lens slider 20. Haptic slider 56' has a pair of bending arms 58 at its rear end. It is substantially Y-shaped. The following description refers to one bending arm 58, but equally applies to both bending arms 58. The end of bending arm 58 is substantially T-shaped herein, so that an outward projection 59 and an inward projection is provided.

FIGS. 16.a and 16.b show haptic slider 56' of FIG. 15 operatively coupled with lens slider 20 and folding body 51. When lens slider 20 is actuated it first encounters haptic slider 56', in particular bending arms 58 thereof. It is also possible for lens slider 20 to be already engaged at haptic slider 56' in its initial position. Lens slider 20 biases the two bending arms 58 against the inner surface of injector body 10, not shown here. In more detail, lens slider 20 biases the outward projections 59 of bending arms 58 against the inner surface of injector body 10. By moving lens slider 20, haptic slider 56' is also moved towards the front end 100a of injector 100. Preferably, haptic slider 56' is intended to be moved only so far that the haptic 91 can be transferred into receptacle area 54. It is then intended to be decoupled or separated from lens slider 20. This is achieved by two recesses 10f, in particular openings, which are formed in the injector body 10 at a position matched to the position of receptacle area 54, into which projections 59 may engage due to the biasing pressure. By this engagement of the projections, haptic slider 56' is decoupled from lens slider 20, and is optionally locked. Lens slider 20, however, may continue to slide forwards through the bifurcation of haptic slider 56', to grab the lens 90 and eject it from injector 100.

FIG. 17 shows the injector 100 together with the haptic slider 56' of FIG. 15. Projections 59 of haptic slider 56', which have come into engagement in openings 10f of injector body 10 and now extend outwardly, are visible herein. In this manner, haptic slider 56' is fixed at its position in the injector 100. It stops, so to speak. It is decoupled from the movement of lens slider 20.

Finally, FIG. 18 shows another embodiment of a folding body 51 having a receptacle area 54 for the trailing haptic 91 of a lens 90. First, receptacle area 54 ends toward the front end 51a in a groove or channel 54-1 formed in the lower end 51d of folding body 51. As a result, the curling-up of trailing haptic 91 into lens 90 is improved. Second, folding body 51 is made of two parts in this case. A kind of base 54-2 is provided in which the actual folding member 54-3 with haptic receptacle area 54 is inserted. Folding member 54-3 is separated from retaining ledges 52 which are integral with the folding body. Retaining ledges 52 are provided by base 54-2.

This configuration provides safety enhancement. The separation into two parts allows to increase the distance between retaining ledges 52 and the lower end 51d of folding rib 51. In this way, jamming of the lens 90 during the folding process can substantially be eliminated. Folding member 54-3 is arranged to be displaceable within base 54-2 towards the upper end 50c. This may for example be achieved by having folding member 54-3 arranged in a manner so that the upper end thereof does not abut on base 54-2 in the interior thereof. An intermediate space is provided. Moreover, a flexible body may be introduced in the intermediate space, for example a foam material. Thereby, a pressure may be exerted on folding member 54-3. Folding member 54-3, when reaching lens 90, may transfer the lens until the bottom of transport channel 31, in particular regardless of the thickness of the lens 90. When impacting on the bottom of transport channel 31, folding member 54-3 may then be pushed further upwards into base 54-2. By advancing plunger 20, folding member 54-3 may be forced to adopt a common roofline with base 54-2. Thereby, a substantially uniform channel is provided which facilitates advancement, for example with a silicone buffer.

It will be apparent to those skilled in the art that the above embodiments have been described by way of example only. The invention is not limited to these embodiments but may be modified in many ways without departing from the spirit of the invention.

Features of individual embodiments may be combined with each other as well as with the features mentioned in the general part of the description.

LIST OF REFERENCE NUMERALS

10 Injector body, or injector housing, or housing, or handset
10a Front end of injector body
10b Rear end of injector body
10c Upper end of injector body
10d Lower end of injector body
10e Slot in injector body
10f Recess or opening in injector body
11 Handle on injector body
12 Recess in injector body
13 Guiding means or guiding rail for slider
14 Hole in injector body
20 Slider, or plunger, or lens slider
20a Front end of slider
20b Rear end of slider
20-1 First portion of slider
20-2 Second, forward portion of slider
21 Handle, or slider handle
22 Slider rod, or slider arm
23 Guiding means for the lens, or fork
24 Receptacle area for haptic of the lens, or recess
25 Projection on slider, or latching lug
30 Cannula, or tube for insertion into the eye, or discharging body for the lens
30a Front end of cannula
30b Rear end of cannula
30c Upper end of cannula
30d Lower end of cannula
31 Transport channel, or advancing channel
32 Lateral inlet opening
33 Lug on cannula, or latching lug
40 Magazine, or container for storing the lens
40a Front end of magazine
40b Rear end of magazine
40c Upper end of magazine
40d Lower end of magazine
41 Cavity, or interior of magazine
42 Bottom of magazine
43 Wall of magazine
44 Receptacle area for a lens and a haptic, or recess in the magazine wall
45 Guiding area and/or receptacle area for a haptic of a lens, or recess, or channel in the magazine wall
47 Recess or opening in the magazine wall
48 Recess or opening in the magazine wall
50 Folding flap, or folding plate support, or flap
50a Front end of folding flap
50b Rear end of folding flap
50c Upper side of folding flap
50d Lower side of folding flap
51 Folding body, or folding plate, or folding rib
51a Front end of folding body
51b Rear end of folding body
51d Lower end of folding plate
52 Retaining ledge on folding plate
52d Lower side of retaining ledge
53 Projection on folding flap
54 Receptacle area, or recess in folding body
54-1 Groove in folding body
54-2 Base of folding body
54-3 Folding member of folding body
55 Stop, or lug on folding body
56 L-shaped haptic slider
56' Y-shaped haptic slider
57 Claw, or gripper on haptic slider
58 Bending arm of haptic slider
59 Projection on bending arm
60 Retainer, or retaining flap, or flap
60c Upper surface of retainer
60d Lower surface of retainer
61 Leg of retainer
62 Opening, or hole in retainer
63 Projection on retaining flap
64 Retaining device, or means for locking or securing the lens, or fixing device
65 Anti-rotation protection, or pin, or projection
66 Intermediate portion, or support, or rib
80 Cartridge, or injection cartridge
90 Lens, or intraocular lens
91 Haptic of the lens
100 Injector, or injector system, or applicator
100a Front end of injector
100b Rear end of injector

The invention claimed is:

1. An injector system for implanting a lens into an eye, said injector system comprising:
an injector body having a front end and a rear end,
a cannula arranged at the front end of the injector body, wherein the cannula provides a transport channel for the lens to be implanted, wherein the lens can be fed into the transport channel via an inlet opening of the transport channel,
a magazine having a retainer for the lens and a receptacle area for the lens, wherein the lens can be secured in the receptacle area via the retainer, wherein the magazine is arranged in a manner so that the lens can be fed into the transport channel via the inlet opening,
a folding body comprising a base and a folding member, wherein the folding member is inserted into the base and/or wherein the folding member is arranged so as to be moveable in the base,
wherein the folding body is insertable into the magazine and into the inlet opening for pushing the lens into the transport channel in such a manner that the lens is at least partially foldable around the folding body, and
a slider that is slideably arranged in the injector body and that can be pushed into the transport channel via the front end of the injector body in such a way that the lens can be ejected from the transport channel.

2. The injector system as claimed in claim 1, wherein the retainer is configured as a flap, wherein in a closed position of the flap, the lens can be secured in the receptacle area.

3. The injector system as claimed in claim 2, wherein the flap is pivotally mounted to the magazine.

4. The injector system as claimed in claim 2, wherein the magazine is push-fittable to the cannula.

5. The injector system as claimed in claim 1, wherein at a side of the retainer that is associated with the lens, the retainer has a retaining device and/or anti-rotation protection for a lens to be stored in the receptacle area.

6. The injector system as claimed in claim 5, wherein the retaining device is formed as a projection at least partially extending over the periphery of the lens to be secured in the receptacle area and having a curvature that substantially corresponds to that of the lens, and/or wherein the anti-rotation protection is configured as at least one pin that engages between the lens arranged in the receptacle area and a haptic of said lens.

7. The injector system as claimed in claim 1, wherein the retainer has an opening, and the folding body is insertable into the magazine and into the inlet opening of the transport channel through said opening in the retainer and/or wherein the folding body is arranged at a lower side of a flap; wherein the flap is pivotally mounted to the cannula in a manner so that, in a hinged-down condition of the flap, the lens is disposed in the transport channel and is folded, at least partially, around the folding body.

8. The injector system as claimed in claim 7, wherein the flap is pivotally mounted to the cannula.

9. The injector system as claimed in claim 1, wherein at least two retaining ledges for the lens are provided at the folding body and/or in the transport channel, wherein the ledges define an engagement surface at least for one edge of the lens upon insertion of the lens into the transport channel.

10. The injector system as claimed in claim 1, wherein the folding body has a receptacle area for a trailing haptic of the lens into which the trailing haptic of the lens can be introduced.

11. The injector system as claimed in claim 10, wherein the receptacle area for the trailing haptic of the lens is in the form of a recess at a rear end of the folding body.

12. The injector system as claimed in claim 1, further comprising a haptic slider for inserting the trailing haptic into the receptacle area of the folding body.

13. The injector system as claimed claim 12, wherein the haptic slider is or can be coupled with the slider for the lens in a manner so that by moving the slider for the lens, the trailing haptic of the lens can be pushed into the receptacle area of the folding body by means of the haptic slider.

14. The injector system as claimed in claim 13, wherein the haptic slider comprises at least one bending arm that is engaged by the slider or that comes in engagement with the slider when pushing out the lens, so that the at least one bending arm is biased against an inner surface of the injector body and the haptic slider is movable together with the slider towards the front end of the injector.

15. The injector system as claimed in claim 14, wherein the at least one bending arm has at least one projection through which the bending arm is biased against the inner surface of the injector body and/or wherein when displacing the haptic slider towards the front end of the injector, the at least one bending arm engages into a recess in the inner surface of the injector body, so that the haptic slider can be decoupled from the slider for the lens.

16. The injector system as claimed in claim 12, wherein the haptic slider, at a front end thereof, has a claw for the trailing haptic of the lens.

17. The injector system as claimed in claim 1, wherein the inlet opening is a lateral inlet opening and/or wherein the slider is axially slideably arranged in the injector body.

18. The injector system as claimed in claim 1, wherein the folding body is provided as a separate component that is separate and distinct from the injector body.

19. The injector system as claimed in claim 1, wherein the folding body is integral with the injector body.

20. An injector system for implanting a lens into an eye, said injector system comprising:
an injector body having a front end and a rear end,
a cannula arranged at the front end of the injector body, wherein the cannula provides a transport channel for the lens to be implanted, wherein the lens can be fed into the transport channel via an inlet opening of the transport channel,
a magazine having a retainer for the lens and a receptacle area for the lens, wherein the lens can be secured in the receptacle area via the retainer, wherein the magazine is arranged in a manner so that the lens can be fed into the transport channel via the inlet opening,
a folding body that is insertable into the magazine and into the inlet opening for pushing the lens into the transport channel in such a manner that the lens is at least partially foldable around the folding body, and
a slider that is slideably arranged in the injector body and that can be pushed into the transport channel via the front end of the injector body in such a way that the lens can be ejected from the transport channel;
wherein the folding body has a stop for a leading haptic of the lens, so that when pushing out the lens via the slider, the leading haptic comes to rest on the lens by means of the stop.

21. The injector system as claimed in claim 20, wherein the stop for the leading haptic of the lens is provided as a lug at a lower end of the folding body.

22. The injector system as claimed in claim 21, wherein the stop for the leading haptic of the lens is provided as a flexible lug at the lower end of the folding body.

23. An injector system for implanting a lens into an eye, said injector system comprising:
an injector body having a front end and a rear end,
a cannula arranged at the front end of the injector body, wherein the cannula provides a transport channel for the lens to be implanted, wherein the lens can be fed into the transport channel via an inlet opening of the transport channel,
a magazine having a retainer for the lens and a receptacle area for the lens, wherein the lens can be secured in the receptacle area via the retainer, wherein the magazine is arranged in a manner so that the lens can be fed into the transport channel via the inlet opening,
a folding body that is insertable into the magazine and into the inlet opening for pushing the lens into the transport channel in such a manner that the lens is at least partially foldable around the folding body, and
a slider that is slideably arranged in the injector body and that can be pushed into the transport channel via the front end of the injector body in such a way that the lens can be ejected from the transport channel;
wherein, at a side of the retainer that is associated with the lens, the retainer comprises anti-rotation protection for a lens that is to be stored in the receptacle area, wherein the anti-rotation protection is configured as at least one pin, wherein the at least one pin engages between the lens and a haptic of the lens, and wherein the anti-rotation protection is arranged at the retaining device.

24. An apparatus for implanting a lens into an eye, said apparatus comprising an injector body, a magazine, a folding body, a retainer, a receptacle area, and a slider, wherein the folding body comprises a base and a folding member, wherein the injector body has a front end and a rear end, wherein a cannula is arranged at the front end of the injector body, wherein the cannula provides a transport channel for the lens to be implanted, wherein the lens can be fed into the transport channel via an inlet opening of the transport channel, wherein the retainer and the receptacle area are constituents of the magazine, wherein the retainer secures the lens in the receptacle area, wherein the magazine is arranged to permit feeding the lens in to the transport channel via the inlet opening, wherein the magazine receives the folding body into the inlet opening, wherein after the folding body has been inserted into the magazine, the folding body pushes the lens into the transport channel and does so in a manner that causes the lens to at least partially fold around the folding body, wherein the slider is arranged to slide in the injector body, wherein when the slider is pushed into the transport channel via the front end of the injector body the lens is ejected from the transport channel, wherein the folding member is inserted in the base of the folding body, and wherein the folding member is arranged so as to be moveable in the base.

\* \* \* \* \*